United States Patent
Huang et al.

(10) Patent No.: US 10,550,104 B2
(45) Date of Patent: *Feb. 4, 2020

(54) PLINABULIN COMPOSITIONS

(71) Applicant: BeyondSpring Pharmaceuticals, Inc., New York, NY (US)

(72) Inventors: Lan Huang, Bronx, NY (US); Aniruddh Singh, Carteret, NJ (US)

(73) Assignee: BeyondSpring Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/212,386

(22) Filed: Dec. 6, 2018

(65) Prior Publication Data
US 2019/0106410 A1    Apr. 11, 2019

Related U.S. Application Data

(63) Continuation of application No. 15/741,635, filed as application No. PCT/US2016/041773 on Jul. 11, 2016, now Pat. No. 10,155,748.

(60) Provisional application No. 62/191,990, filed on Jul. 13, 2015.

(51) Int. Cl.
*C07D 403/06* (2006.01)
*B01D 9/00* (2006.01)

(52) U.S. Cl.
CPC ......... *C07D 403/06* (2013.01); *B01D 9/0045* (2013.01); *B01D 9/0054* (2013.01); *B01D 9/0063* (2013.01); *B01D 2009/0086* (2013.01); *C07B 2200/13* (2013.01)

(58) Field of Classification Search
CPC .................................................. C07D 403/06
See application file for complete search history.

(56) References Cited

U.S. PATENT DOCUMENTS

| | | | |
|---|---|---|---|
| 4,535,183 A | 8/1985 | Kneen | |
| 5,607,934 A | 3/1997 | Tone et al. | |
| 5,733,888 A | 3/1998 | Carver et al. | |
| 5,852,018 A | 12/1998 | Bryans et al. | |
| 5,872,151 A | 2/1999 | Rhodes | |
| 5,874,443 A | 2/1999 | Kiely et al. | |
| 5,886,210 A | 3/1999 | Rayle et al. | |
| 5,891,877 A | 4/1999 | Brocchini et al. | |
| 5,922,683 A | 7/1999 | Or et al. | |
| 5,939,098 A | 8/1999 | Reidenberg et al. | |
| 5,958,980 A | 9/1999 | Rhodes | |
| 6,069,146 A | 5/2000 | Fenical et al. | |
| 6,350,759 B1 | 2/2002 | Casara et al. | |
| 6,358,957 B1 | 3/2002 | Fukumoto et al. | |
| 6,500,825 B2 | 12/2002 | Lan et al. | |
| 6,506,787 B2 | 1/2003 | Fujishita et al. | |
| 6,509,331 B1 | 1/2003 | Audia et al. | |
| 6,583,143 B2 | 6/2003 | Haddach | |
| 6,713,480 B2 | 3/2004 | Fukumoto et al. | |
| 6,808,710 B1 | 10/2004 | Wood et al. | |
| 6,972,289 B1 | 12/2005 | Kanzaki et al. | |
| 7,026,322 B2 | 4/2006 | Hayashi et al. | |
| 7,064,201 B2 | 6/2006 | Hayashi et al. | |
| 7,488,802 B2 | 2/2009 | Collins et al. | |
| 7,629,380 B2 | 12/2009 | McMorris et al. | |
| 7,635,757 B2 | 12/2009 | Freeman et al. | |
| 7,674,903 B2 | 3/2010 | Hayashi et al. | |
| 7,700,615 B2 | 4/2010 | Edwards et al. | |
| 7,919,497 B2 | 4/2011 | Palladino et al. | |
| 7,943,743 B2 | 5/2011 | Korman et al. | |
| 7,956,058 B2 | 6/2011 | Hayashi et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 2002/0028819 A1 | 3/2002 | Teng et al. | |
| 2002/0143021 A1 | 10/2002 | Fukumoto et al. | |
| 2004/0102454 A1 | 5/2004 | Hayashi et al. | |
| 2005/0090667 A1 | 4/2005 | Hayashi et al. | |
| 2005/0197344 A1 | 9/2005 | Palladino et al. | |
| 2006/0079534 A1 | 4/2006 | Kanzaki et al. | |
| 2006/0167010 A1 | 7/2006 | Hayashi et al. | |
| 2006/0217553 A1 | 9/2006 | Hayashi et al. | |
| 2006/0223822 A1 | 10/2006 | Hayashi et al. | |
| 2006/0223823 A1 | 10/2006 | Hayashi et al. | |
| 2007/0078138 A1 | 4/2007 | Palladino et al. | |
| 2007/0293453 A1 | 12/2007 | Fisher et al. | |
| 2008/0221122 A1 | 9/2008 | Palladino et al. | |
| 2008/0255035 A1 | 10/2008 | Trieu et al. | |
| 2009/0170837 A1 | 7/2009 | Gourdeau et al. | |
| 2009/0317368 A1 | 12/2009 | Chen | |
| 2012/0277251 A1 | 11/2012 | Palladino et al. | |
| 2013/0303481 A1 | 11/2013 | Marcus | |

(Continued)

FOREIGN PATENT DOCUMENTS

CA    2 403 790 A1    7/2001
EP    0 054 924 A2    6/1982

(Continued)

OTHER PUBLICATIONS

Abels, Christoph, Targeting of the Vascular System of Solid Tumours by Photodynamic Therapy (PDT), Photochem Photobiol Sci., (Mar. 2004) 3: 765-771.
Abstracts of The 1999 Joint Chubu and Kansai Branch Conference and Symposia of Japan Society for Bioscience, Biotechnology, and Agrochemistry, (1999) p. 48.
Acquaviva et al., "Targeting KRAS-Mutant Non-Small Cell Lung Cancer with the Hsp90 Inhibitor Ganetespib", Mol Cancer Ther, Dec. 2012, 11(12), pp. 2633-2643.
Aggarwal et al., Antiangiogenic agents in the management of non-small cell lung cancer: Where do we stand now and where are we headed? Cancer Biology & Therapy (2012), 13(5), 247-263.
Ahmed et al. "A new rapid and simple non-radioactive assay to monitor and determine the proliferation of lymphocytes: an alternative to [³H]thymidine incorporation assay." J. Immunol. Methods. 170, 211-224 (1994).

(Continued)

*Primary Examiner* — Bruck Kifle
(74) *Attorney, Agent, or Firm* — Knobbe, Martens, Olson & Bear, LLP

(57) ABSTRACT

Disclosed herein are plinabulin polymorphs, compositions, their use and preparation as therapeutic agents. In particular, some embodiments relate to plinabulin monohydrate in a crystalline form.

20 Claims, 24 Drawing Sheets

(56) References Cited

U.S. PATENT DOCUMENTS

| | | |
|---|---|---|
| 2015/0291549 A1 | 10/2015 | Chupak et al. |
| 2016/0250209 A1 | 9/2016 | Huang |
| 2018/0028531 A1 | 2/2018 | Huang et al. |
| 2018/0036304 A1 | 2/2018 | Huang |
| 2018/0042921 A1 | 2/2018 | Huang |
| 2019/0000841 A1 | 1/2019 | Huang |

FOREIGN PATENT DOCUMENTS

| | | |
|---|---|---|
| EP | 0655060 B1 | 1/1998 |
| EP | 1264831 A1 | 12/2002 |
| GB | 2143823 | 2/1985 |
| JP | 5009164 | 1/1993 |
| JP | H05255106 | 10/1993 |
| JP | 10130266 | 5/1998 |
| JP | 2002-507612 A | 3/2002 |
| JP | 2007-520565 A | 7/2007 |
| JP | 2016-536352 A | 11/2016 |
| JP | 2018-5201178 A | 7/2018 |
| KR | 10-2018-0027563 A | 3/2018 |
| RU | 2011 148 945 A | 4/2010 |
| RU | 2662298 C2 | 7/2018 |
| WO | WO 87/05297 | 9/1987 |
| WO | WO 94/07479 | 4/1994 |
| WO | WO 95/06077 A2 | 3/1995 |
| WO | WO 1995/21832 | 8/1995 |
| WO | WO 1996/20190 | 7/1996 |
| WO | WO 1999/38844 | 8/1999 |
| WO | WO 1999/048889 | 9/1999 |
| WO | WO 2001/053290 | 7/2001 |
| WO | WO 2001/070663 A2 | 9/2001 |
| WO | WO 2004/054498 A2 | 7/2004 |
| WO | WO 2004/054498 A3 | 7/2004 |
| WO | WO 2005/077940 | 8/2005 |
| WO | WO 2006/121168 A1 | 11/2006 |
| WO | WO 2009/089260 A2 | 7/2009 |
| WO | WO 2010/001169 A2 | 1/2010 |
| WO | WO 2011/066389 A1 | 6/2011 |
| WO | WO 2011/109625 A1 | 9/2011 |
| WO | WO 2011/146382 A1 | 11/2011 |
| WO | WO 2011/151423 A1 | 12/2011 |
| WO | WO 2012/014549 | 2/2012 |
| WO | WO 2012/035436 A1 | 3/2012 |
| WO | WO 2012/145493 A1 | 10/2012 |
| WO | WO 2013/090552 A1 | 6/2013 |
| WO | WO 2014/066834 A1 | 5/2014 |
| WO | WO 2014/160183 | 10/2014 |
| WO | WO 2014/195852 A1 | 12/2014 |
| WO | WO 2015/051543 A1 | 4/2015 |
| WO | WO 2015/160641 A2 | 10/2015 |
| WO | WO 2016/130839 A1 | 8/2016 |
| WO | WO 2016/144635 A1 | 9/2016 |
| WO | WO 2016/144636 A1 | 9/2016 |
| WO | WO 2017/011399 A1 | 1/2017 |
| WO | WO 2017/139231 A1 | 8/2017 |
| WO | WO 2017/214052 A1 | 12/2017 |
| WO | WO 2018/129381 A1 | 7/2018 |
| WO | WO 2018/144764 A1 | 8/2018 |
| WO | WO 2018/169887 A1 | 9/2018 |

OTHER PUBLICATIONS

Akerlund et al., "Diketopiperazine-Based Polymers from Common Amino Acids," Journal of Applied Polymer Science, (2000) 78 (12), 2213-2218.

Algaier et al. "The effects of dimethyl sulfoxide on the kinetics of tubulin assembly." Biochim. Biophys. Acta. 954, 235-43 (1988).

Ali et al. "Toxicity of echinulin from Aspergillus chevalieri in rabbits." Toxicology Letters. (1989) 48: 235-41.

Asahina, T., "Spectrochemical Study of Amino-acid Anhydrides," Bulletin of the Chemical Society of Japan, (1930) 5, 354-365.

Augustin, M. "Die Umsetzung des 2,5-Diketopiperazins mit Aldehyden und Nitrosoverbindungen" Journal für Praktische Chemie, (1966) 32(4), 158-166.

Bankowska et al., Derivatives of 1,2,3-triazole. Potential drugs?, Wiadomosci Chemiczne (2012), 66(11-12), 993-1022.

Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11: 1411-1415.

Bertelsen et al., Vascular effects of plinabulin (NPI-2358) and the influence on tumour response when given alone or combined with radiation, International Journal of Radiation Biology (2011),87(11), 1126-1134.

Bertino J., et al., "Principles of Cancer Therapy." Cecil Textbook of Medicine. Eds. Lee Goldman, et al. 21nd ed., (2000), Chapter 198, pp. 1060-1074.

Bond et al. "The Synthesis of Viridamine, a Penicillium Viridicatum Mycotoxin." Synthetic Commun. 19 (13&14), 2551-2566 (1989).

Borisy, G.G. "A Rapid Method for Quantitative Determination of Microtubule Protein using DEAE-Cellulose Filters." Anal. Biochem. 50, 373-385 (1972).

Burtles, Sally, "Transition from Preclinical to first-in-man Phase", Expert Scientific Group on Phase One Clinical Trials Final Report, Presentation Jun. 19, 2006, pp. 35-38.

Cai, Sui X., "Small Molecule Vascular Disrupting Agents: Potential New Drugs for Cancer Treatment", Recent Pat Anticancer Drug Discov. (2007) 2(1): 79-101.

Chaplin et al., "Antivascular approaches to solid tumour thereapy: evaluation of tubulin binding agents", Br. J. Cancer 1996, 74 (Suppl. XXVII), S86-S88.

Cole, P., "DURVALUMAB, Human anti-PD-L1 monoclonal antibody Immune checkpoint inhibitor Oncolytic", Drugs of the Future 2014, 39(12): pp. 843-847.

Cui et al. "Novel Mammalian Cell Cycle Inhibitors, Tryprostatins A, B and Other Diketopiperazines Produced by Aspergillus fumigatus." J. Antibiotics. 49(6): 527-33 (1996).

Cui et al. "Novel Mammalian Cell Cycle Inhibitors, Tryprostatins A, B and Other Diketopiperazines Produced by Aspergillus fumigatus." J. Antibiotics. 49(6), 534-40 (1996).

Dandan et al., JP 5009164, Chemical Abstract 119: 8514 (1993).

Davis et al., ZD6126: A Novel Vascular-targeting Agent That Causes Selective Destruction of Tumor Vasculature, Cancer Research (Dec. 15, 2002) 62: 7247-7253.

Dörwald, F., "Side Reactions in Organic Synthesis" Wiley-VCH Verlag GmbH & Co. KgaA, Weinheim, (2005), book cover and preface p. IX only.

Drug Approval and Licensing Procedures in Japan 2001, 2001, pp. 243-244.

Ferrer et al., Plinabulin: tubulin polymerization inhibitor vascular-disrupting agent oncolytic, Drugs of the Future (2010), 35(1), 11-15.

Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.

Frost et al., Novel Syngeneic Pseudo-orthotopic Prostate Cancer Model: Vascular, Mitotic and Apoptotic Responses to Castration, Microvasc Research (Dec. 2004) 69: 1-9.

Fukushima et al., "Biological Activities of Albonoursin," J. Antibiotics, (1973) 26:175.

Gallina et al., "Condensation of 1,4-diacetylpiperazine-2,5-dione with aldehydes", Tetrahedron 1974, 30, 667-673.

Goldani et al. "Treatment of murine pulmonary mucormycosis with SCH 42427, a broad-spectrum triazole antifungal drug", Correspondence, J Antimicrob Chemother. 33, 369-372 (1994).

Goldfarb et al., "Synthesis of β-2-thienylalanine," Izvestiya Akademii Nauk SSSR, Seriya Khimicheskaya, (1958) 98-100, as abstracted by CAPLUS.

Gordon et al. "Reductive Alkylation on a Solid Phase: Synthesis of a Piperazinedione Combinatorial Library." J. Bioorg. Med. Chem. Letters. 5, 47-50 (1995).

Granville et al., Release of Cytochrome c1 Bax Migration, Bid Cleavage, and Activation of Caspases 2, 3, 6, 7, 8, and 9 during Endothelial Cell Apoptosis, Am J Path., (Oct. 1999) 155(4): 1021-1025.

Gridelli et al., Vascular disrupting agents: a novel mechanism of action in the battle against non-small cell lung cancer, Oncologist (2009), 14(6), 612-620.

(56) References Cited

OTHER PUBLICATIONS

Gura, Trisha, "Cancer Models: Systems for Identifying New Drugs are Often Faulty", Science 7(Nov. 1997) 278(5340): 1041-1042.
Hamel, E. "Antimitotic Natural Products and Their Interactions with Tubulin." Med. Res. Rev. (1996) 16(2): 207-31.
Hartwell et al. "Checkpoints: Controls that Ensure the Order of Cell Cycle Events." Science. 246, 629-34 (1989).
Hayakawa, Structure-activity relationship analysis, Gan to Kagaku Ryoho (2004), 31(4), 526-528.
Hayashi et al., "Total Synthesis of Anti-microtubule Diketopiperazine Derivatives: Phenylahistin and Aurantiamine," J. Org. Chem., (2000) 65: 8402-8405.
Hayashi et al., Small peptide-based medicinal chemistry for intractable disease, Peptide Science (2009), Volume Date 2008, 45th, 139-140.
Hayashi et al., Medicinal chemistry and chemical biology of diketopiperazine-type antimicrotubule and vascular-disrupting agents, Chemical & Pharmaceutical Bulletin (2013), 61(9), 889-901.
Heist, R. et al. 2014 "Randomized phase 2 trial of plinabulin (NPI-2358) plus docetaxel in patients with advanced non-small cell lung cancer (NSCLC)." J. Clin. Oncol. vol. 32, No. 5s, (suppl; abstr 8054).
Helleman et al. "The International Journal of Biochemistry & Cell Biology," vol. 42, pp. 25-30 (2010).
Horak et al. "Structures of the Austalides A-E, Five Novel Toxic Metabolites from Aspergillus ustus." J Chem Soc Chem Commun. (1981) 1265-67.
http://scienceandresearch.homeoffice.gov.uk/animal-research/publications-and-reference/001-abstracts/abstracts2-2006/02november-2006/457?view=Html; "Abstract #457, Animals in Scientific Procedures (2006)"; (accessed on Nov. 19, 2008).
Hyun et al., "Valine dehydrogenase from Streptomyces albus: gene cloning, heterologous expression and identification of active site by site-directed mutagenesis," FEMS Microbiology Letters (Jan. 1, 2000) 182: 29-34.
Iwasaki, S. "Antimitotic Agents: Chemistry and Recognition of Tubulin Molecule." Med Res Rev. (1993) 13: 183-198.
Iwasaki, S. "Bioactive Natural Products Interfering with Microtubule Function." Kagaku to Seibutsu. 32(3): 153-159 (1994).
Ji et al., Tubulin Colchicine Binding Site Inhibitors as Vascular Disrupting Agents in Clinical Developments, Current Medicinal Chemistry (2015), 22(11), 1348-1360.
Johnson et al. "Kinetic Analysis of Microtubule Self-assembly in Vitro." J. Mol. Biol. 117, 1-31 (1977).
Jure-Kunkel M. et al., "Synergy between chemotherapeutic agents and CTLA-4 blockade in preclinical tumor models", Cancer Immunol. Immunother. 2013, vol. 62, pp. 1533-1545.
Kamb, Alexander, "What's wrong with our cancer models?", Nature Reviews Drug Discovery (Feb. 2005) 4: 161-165.
Kanoh et al., "(−)-Phenylahistin: A New Mammalian Cell Cycle Inhibitor Produced by Aspergillus Ustus," Bioorganic & Medicinal Chemistry Letters, (1997) 7: 2847-2852.
Kanoh et al., "(−)-Phenylahistin Arrests Cells in Mitosis by Inhibiting Tubulin Polymerization," The Journal of Antibiotics, (1999) 52: 134-141.
Kanoh et al., "Antitumor Activity of Phenylahistin in Vitro and in Vivo," Bioscience Biotechnology Biochemistry, (1999) 63(6): 1130-1133.
Kanoh et al., "Synthesis and Biological Activities of Phenylahistin Derivatives," Bioorganic & Medicinal Chemistry, (1999) 7: 1451-1457.
Kanthou et al., Microtubule depolymerizing vascular disrupting agents: novel therapeutic agents for oncology and other pathologies, International Journal of Experimental Pathology(2009), 90(3), 284-294.
Kanzaki et al., "Enzymatic Synthesis of Physiologically Active Substances Utilizing a Novel System for the Synthesis of Diketopiperazines Comprising Dehydroamino Acids as Constituents," Abstracts of Papers Presented at the 1999 Meeting of the Society for Actinomycetes Japan, (1999) 42 (Abstract Only).
Kobayashi et al., "Microtubule Assembly Regulators of Microbial Origin," Abstract of Paper Read at the 1989 Symposium on the Chemistry of Natural Products, (1989) 51.
Kola et al., "Can the pharmaceutical industry reduce attrition rates?", Nature Reviews Drug Discovery (2004) 3: 711-715.
Kondoh et al. "Effects of Tryprostatin Derivatives on Microtubule Assembly In Viro and In Situ." J. Antibiotics. 51, 801-04 (1998).
Kopple et al., "A Convenient Synthesis of 2,5-Piperazinediones1a," The Journal of Organic Chemistry, (1967) 33: 862-864.
Kreamer K., "Immune checkpoint blockade: A New Paradigm in Treating Advanced Cancer", J. Adv. Pract. Oncol., 2014, vol. 5, pp. 418-431.
Krishan, A. "Rapid Flow Cytofluorometric Analysis of Mammalian Cell Cycle by Propidium Iodide Staining." J. Cell Biol. 66, 188-193 (1975).
Küster & Koeppenhöfer, "Über eininge Pyrrolderivate," Z. Physiol, Chem., (1927) 172:126-137.
Kupchan et al. "Steganacin and Steganangin, Novel Antileukemic Lignan Lactones from Steganotaenia araliacea 1-3." J. Am. Chem. Soc. (1973) 95(4): 1335-36.
Lacey et al. "Interaction of Phomopsin A and Related Compounds with Purified Sheep Brain Tubulin." Biochem. Pharmacol. 36, 2133-38 (1987).
Laemmli, U.K. "Cleavage of Structural Proteins during the Assembly of the Head of Bacteriophage T4." Nature. 227, 680-85 (1970).
Larsen et al. "Aurantiamine, A Kiketopiperazine from Two Varieties of Penicillium Aurantiogriseum." Phytochemistry. 31, 1613-1615 (1992).
Leaf, Clifton, "Why are we losing the war on cancer (and how to win it)?", Health Administrator (2005) XVII(1): 172-183.
Lee et al. "The Reconstitution of Microtubules from Purified Calf Brain Tubulin." Biochemistr. 14(23), 5183-87 (1975).
Lee et al., Colchicine site inhibitors of microtubule integrity as vascular disrupting agents, Drug Development Research (2008), 69(6), 352-358.
Li, Y., et al. "Interaction of marine toxin dolastatin 10 with porcine brain tubulin: competitive inhibition of rhizoxin and phomopsin A binding." Chem. Biol. Interact. 93, 175-83 (1994).
Liwo et al. "Origin of the Ring-Ring Interaction in Cyclic Dipeptides Incorporating an Aromatic Amino Acid." Tetrahedron Lett. 26, 1873-1876 (1985).
Luduena, R.F. "Contrasting Roles of Tau and Microtubule-associated Protein 2 in the Vinblastine-induced Aggregation of Brain Tubulin." J. Biol. Chem. 259:12890-98 (1984).
Mahindroo et al., "Antitubulin Agents for the Treatment of Cancer—A Medicinal Chemistry Update", Expert Opin. Ther. Patents (2006) 16(5): 647-691.
Millward et al., "Phase 1 study of the novel vascular disrupting agent plinabulin (NPI-2358) and docetaxel," The Journal of New Anticancer Agents, vol. 3, No. 30, Feb. 16, 2011 plinabulin (NPI-2358) and docetaxel, Investigational New Drugs (2012), 30(3), 1065-1073.
Mita et al., Phase 1 First-in-Human Trial of the Vascular Disrupting Agent Plinabulin(NPI-2358) in Patients with Solid Tumors or Lymphomas, Clinical Cancer Research (2010), 16(23), 5892-5899.
Mita et al., "Phase II study of docetaxel with or without plinabulin (NPI-2358) in patients with non-small cell lung cancer (NSCLC)", J. Clin. Oncol., 2010, vol. 28, No. 15 supplement, p. 7592.
Neidle, Stephen, ed., Cancer Drug Design and Discovery , 9th Edition, Elsevier/Academic Press, (2008) Chapter 18, pp. 427-431.
Nema et al., Excipients and Their Role in Approved Injectable Products: Current Usage and Future Directions, PDA J Pharm Sci and Tech 2011, 65 287-332.
Nicholson et al., NPI-2358 is a tubulin-depolymerizing agent: in-vitro evidence for activity as a tumor vascular-disrupting agent, Anti-Cancer Drugs (2005), Volume Date 2006, 17(1), 25-31.
Niemann et al, "The Synthesis of the Three Isomeric dl-β-Pyridylalanines" Journal of the American Chemical Society, (1942) 64(7):1678-1682.
Nihei et al., "Evaluation of antivascular and antimitotic effects of tubulin binding agents in solid tumor therapy", Jpn. J. Cancer. Res. 1999, 90, 1387-1395.

(56) References Cited

OTHER PUBLICATIONS

Nitecki et al., "A Simple Route to Sterically Pure Diketopiperazines1," The Journal of Organic Chemistry, (1968) 33:864-866.
Paik et al., "A Phase 2 Study of Weekly Albumin-Bound Paclitaxel (Abraxane®) Given as a Two-Hour Infusion", Cancer Chemother. Pharmacol., Nov. 2011, vol. 68, No. 5, pp. 1331-1337.
Perez, Edith A., "Paclitaxel in Breast Cancer," The Oncologist, 1998, vol. 3, pp. 373-389.
Petrillo et al., Novel VEGF-independent strategies targeting tumor vasculature: clinical aspects, Current Pharmaceutical Design (2012), 18(19), 2702-2712.
Pettit et al. "Antineoplastic Agents. 291. Isolation and Synthesis of Combretastatins A-4, A-5, and A-6 1a." J. Med. Chem. (1995) 38: 1666-1672.
Prior, I. et al. 2012 "A Comprehensive Survey of Ras Mutations in Cancer" Cancer Res. vol. 72, No. 10, pp. 24570-2467.
Roberge et al. "Antitumor Drug Fostriecin Inhibits the Mitotic Entry Checkpoint and Protein Phospatases 1 and 2A." Cancer Res. 54, 6115-21 (1994).
Roberts et al, "Trends in the Risks and Benefits to Patients with Cancer Participating in Phase 12 Clinical Trials", JAMA (2004) 292(17): 2130-2140.
Rowinsky et al. "Taxol: A Novel Investigational Antimicrotubule Agent." J. Natl. Cancer Inst. 82(15): 1247-59 (1990).
Rowinsky et al, "The clinical pharmacology and use of antimicrotubule agents in cancer chemotherapeutics", Pharmacol. Ther. 1991, 52, 35-84.
Sackett, D.L. "Podophyllotoxin, Steganacin and Combretastatin: Natural Products that Bind at the Colchicine Site of Tubulin." Pharmacol. Ther. (1993) 59: 163-228.
Saito et al., "Synthesis of novel octahydro-1, 5-imino-3-benzazocin-4, 7, 10-trione derivatives having a methyl group at the C-2 position as ABC ring models of saframycins," Chemical & Pharmaceutical Bulletin (1997) 45(7):1120-1129.
Scholl et al., "Synthetic Lethal Interaction between Oncogenic KRAS Dependency and the STK33 Suppression in Human Cancer Cells", Cell 137, May 29, 2009, pp. 821-834.
Sezaki et al., "Drug Delivery Systems", Drug Development, (Jul. 1989) 13: 116, Table 2. 29.
Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.
Shen et al., Time- and dose-dependent vascular changes induced by the novel vascular disrupting drug NPI-2358 in a murine cancer model monitored with DCE-MRI, U.S. Chinese Journal of Lymphology and Oncology(2010), 9(4), 151-153.
Sherline et al. "Binding of Colchicine to Purifiied Microtubule Protein." J. Biol. Chem. 250, 5481-86 (1975).
Shi, Q et al, "Recent progress in the development of tubulin inhibitors as antimitotic antitumor agents", Curr. Pharm. Des. 1998, 4, 219-248.
Singh et al., A novel vascular disrupting agent plinabulin triggers JNK-mediated apoptosis and inhibits angiogenesis in multiple myeloma cells, Blood (2011), 117(21), 5692-5700.
Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.
Smedsgaard et al. "Using direct electrospray mass spectrometry in taxonomy and secondary metabolite profiling of crude fungal extracts." J. Microbiol. Meth. (1996) 25: 5-17.
Sölter et al., Barettin, Revisited? Tetrahed Lttrs. (Mar. 2002) 43: 3385-3386.
Spear et al., Vascular disrupting agents (VDA) in oncology: advancing towards new therapeutic paradigms in the clinic, Current Drug Targets (2011), 12(14), 2009-2015.
Stein, J., ed. "Internal Medicine," Fourth Edition, Mosby-Year Book, Inc., (1994), Chapters 71-72, pp. 699-729.
Steyn, P.S. "The Structures of Five Diketopiperazines from Aspergillus Ustus." Tetrahedron. 29, 107-120 (1973).

Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).
Takahashi et al. "Rhizoxin binding to tubulin at the maytansine-binding site." Biochim. Biophys. Acta. 926, 215-23 (1987).
Talmadge et al., Murine models to evaluate novel and conventional therapeutic strategies for cancer., Am J Pathol, 2007, vol. 170, Issue 3, pp. 793-804.
Thorpe, Philip E., "Vascular Targeting Agents as Cancer Therapeutics," Clinical Cancer Research, vol. 10, 415-427, Jan. 15, 2004.
Tiwari et al. "A pH- and Temperature-Dependent Cycling Method that doubles the Yield of Microtubule Protein." Anal. Biochem. 215, 96-103 (1993).
Tozer et al., Tumour vascular disrupting agents: combating treatment Resistance, British Journal of Radiology (2008), 81(Spec. Iss. 1), S12-S20.
Turner et al. "Recent Advances in the Medicinal Chemistry of Antifungal Agents." Current Pharmaceutical Design. 2, 209-224 (1996).
Usui et al. "Tryprostatin A, a specific and novel inhibitor of microtubule assembly." Biochem J. 333, 543-48 (1998).
Van der Waerden, B.L., "Wirksamkeits- und Konzentrationsbestimmung durch Tierversuche." Arch Exp Pathol Pharmakol. 195, 389-412, (1940).
Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).
Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.
Wang, T. et al. 1998 "Microtubule interfering agents activate c-Jun N-terminal kinase/stress-activated protein kinase through both Ras and apoptosis signal-regulating kinase pathways". J Biol Chem. vol. 273, No. 9, pp. 4928-4936.
Weisenberg et al. "The Colchicine-Binding Protein of Mammalian Brain and its Relation to Microtubules." Biochemistry (1968) 7(12): 4466-79.
Wilt et al. "Anal cancer in Alaska; a retrospective study of incidence, treatment, and outcomes". Alaska Med Jul.-Sep. 2002; 44(3):56-9, 62.
Yahara et al. "Microtubule Organization of Lymphocytes and its Modulation by Patch and Cap Formation." Cell. 15, 251-259 (1978).
Yamazaki et al. "Crystal Structure and Absolute Configuration of Fumitremorgin B, a Tremorgenic Toxin from Aspergillus Fumigatus Fres." Tetrahedron Lett. 1, 27-28 (1975).
Yamazaki et al. "Synthesis and Structure-Activity Relationship Study of Antimicrotubule Agents Phenylahistin Derivatives and a Didehydropiperazine-2,5-dione Structure", Journal of Medicinal Chemistry, 2012, vol. 55, No. 3, pp. 1056-1071.
Yamazaki et al., Drug discovery study on cyclic dipeptides anti-cancer drugs and chemical biological development, Idenshi Igaku Mook (2012), 21(Saishin Pepuchido Gosei Gijutsu to Sono Soyaku Kenkyu eno Oyo), 260-266.
Yamori T., "A Human Cell Line Panel for Screening Anti-Cancer Drugs", Jap. J. Cancer Chemother. 24, 129-35 (1997).
Yin et al., "Human Mutations That Confer Paclitaxel Resistance," Mol. Cancer Ther. vol. 9(2), pp. 327-335 (2010).
Yokoi et al, "Neihumicin, A New Cytotoxic Antibiotic From Micromonospora Neihuensis," The Journal of Antibiotics, (Apr. 1988) 41(4):494-501.
Yoshida, M.M. Protein Nucleic Acid Enzymes. 38, 1753-1765 (1993).
Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).
Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.

(56) References Cited

OTHER PUBLICATIONS

Zou et al., Effect of Interleukin-1 Blockers, CK112, and CK116 on Rat Experimental Choroidal Neovascularization In Vivo and Endothelial Cell Cultures In Vitro, J Ocul Pharma Thera., (2006) 22(1): 19-25.
Notification of Transmittal of International Preliminary Report on Patentability dated May 23, 2017 for International Patent Application No. PCT/US2016/041773.
Aviel-Ronen et al., "K-ras Mutations in Non-Small-Cell Lung Carcinoma: A Review," Clinical Lung Cancer (Jul. 2006) vol. 8, No. 1, pp. 30-38.
Beavis et al., "Dual PD-1 and CTLA-4 Checkpoint Blockade Promotes Antitumor Immune Responses through CD4+Foxp3- Cell-Mediated Modulation of CD103+ Dendritic Cells," Cancer Immunol Res (Sep. 2018) 6(9):1069-1081.
Blayney et al., "Plinabulin, a Novel Small Molecule That Ameliorates Chemotherapy-Induced Neutropenia, is Administered on the Same Day of Chemotherapy and Has Anticancer Efficacy", Meeting Info.: 58th Annual Meeting and Exposition of the American Society-of-Hematology (ASH), Blood (2016) 128(22): 2508.
Brahmer et al., "Safety and Activity of Anti-PD-L1 Antibody in Patients with Advanced Cancer," N Engl J Med (2012) 366:2455-2465.
Cai, Small molecule vascular disrupting agents: potential new drugs for cancer treatment, a 2009 update, Frontiers in Anti-Cancer Drug Discovery (2010), 1, 380-427.
Callahan et al., "At the Bedside: CTLA-4- and PD-1-blocking antibodies in cancer immunotherapy", J Leukocyte Biol, vol. 94, Jul. 2013, pp. 41-53.
Cooper et al., "Response to BRAF Inhibition in Melanoma is Enhanced When Combined with Immune Checkpoint Blockade," Published OnlineFirst Apr. 29, 2014; DOI: 10.1158/2326-6066.CIR-13-0215; Cancer Immunol Res (Jul. 2014) 2(7) 643-654.
Costa et al., "Analyses of selected safety endpoints in phase 1 and late-phase clinical trials of anti-PD-1 and PD-L1 inhibitors: prediction of immune-related toxicities," Oncotarget (2017) vol. 8, No. 40, pp. 67782-67789.
Garris et al., "Successful Anti-PD-1 Cancer Immunotherapy Requires T Cell-Dendritic Cell Crosstalk Involving the Cytokines IFN-( and IL-12," Immunity (Dec. 18, 2018) 49, pages 1-14, e1-e7 (22 pages).
Heist et al., "Abstract C30: Phase 1/2 study of the vascular disrupting agent (VCA) plinabulin (NPI-2358) combined with docetaxel in patients with non-small cell lung cancer (NSCLC)," Mol. Cancer Ther., 2009; 8(12 Suppl):C30, 2 pages.
Heist et al., "Randomized Phase 2 Trial of Plinabulin (NPI-2358) Plus Docetaxel in Patients with Advanced Non-Small Lung Cancer (NSCLC)," 2014 ASCO Annual Meeting . . . (abstr 8054) Poster Presentation. Retrieved from the internet Jul. 17, 2017: <http://meetinglibrary.asco.org/record/92548/poster>.
Kanzaki et al., "Novel Cyclic Dipeptide Dehydrogenase and Assay Method for Its Activity," Scientific Reports of the Faculty of Agriculture, Okayama University, (1999) 88: 7-11.
Kanzaki et al., "Enzymatic dehydrogenation of cyclo(L-Phe-L-Leu) to a bioactive derivative, albonoursin," Journal of Molecular Catalysis B: Enzymatic (1999) 6(3): 265-270.
Kanzaki et al., "Effective Production of Dehydro Cyclic Dipeptide Albonoursin Exhibiting Pronuclear Fusion Inhibitory Activity, I. Taxonomy and Fermentation," The Journal of Antibiotics, (1999) 52: 1017-1022.
Kanzaki et al., "Effective Production of Dehydro Cyclic Dipeptide Albonoursin Exhibiting Pronuclear Fusion Inhibitory Activity, II. Biosynthetic and Bioconversion Studies," The Journal of Antibiotics, (2000) 53(1): 58-62.
Kanzaki et al., A Novel Potent Cell Cycle Inhibitor Dehydrophenylahistin-Enzymatic Synthesis and Inhibitory Activity toward Sea Urchin Embryo, The Journal of Antibiotics, (Dec. 2002) 55(12): 1042-1047.
Keepers et al. "Comparison of the Sulforhodamine B Protein and Tetrazolium (MTT) Assays for in vitro Chemosensitivity Testing." Eur. J. Cancer. 27, 897-900 (1991).
Kim et al. "Polymer attached cyclic peptides, tetrahedron: Asymmetry." 3(11):1421-1430 (1992).
Kingston, Tubulin-Interactive Natural Products as Anticancer Agents, Journal of Natural Products (2009), 72(3), 507-515.
Kingston, Correction to Tubulin-interactive natural products as anticancer agents, Journal of Natural Products (2011), 74(5), 1352.
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) 21(7) 1639-1651.
Lloyd et al., Abstract A07: Plinabulin: Evidence for an immune-mediated mechanism of action, In: Proceedings of the AACR Special Conference: Function of Tumor Microenvironment in Cancer Progression; Jan. 7-10, 2016; San Diego, CA. Philadelphia (PA): AACR; Cancer Research. Aug. 2016. 76(15 Supp.): abstract nr A07.
Lyman et al., "Risk Models for Predicting Chemotherapy-Induced Neutropenia," The Oncologist (2005) 10:427-437.
Millward et al., "Phase I trial of NPI-2358 (a novel vascular disrupting agent) plus docetaxel," J. Clin. Oncol. (May 2009) 27(15S): 3571-3571, Abstract.
Mita et al., Randomized Phase 2 Study of Docetaxel +/– Plinabulin (NPI-2358) in Patients with Non-Small Cell Lung Cancer (NSCLC), Poster Presentation at ACS Annual '10 Meeting (Jun. 4-8, 2010) 1 page.
Mitsudomi et al., "Mutations of ras genes distinguish a subset of non-small-cell lung cancer cell lines from small-cell lung cancer cell lines," Oncogene (Aug. 1991) vol. 6, No. 8, pp. 1352-1362.
Mohanlal et al., "The plinabulin/docetaxel combination to mitigate the known safety concerns of docetaxel," J Clin Oncol (2016) 34(15_suppl), Abstract e20595.
Neuteboom et al., "450 Poster NPI-2358, a novel tumor vascular disrupting agent potentiates the anti-tumor activity of docetaxel in the non small cell lung cancer model MV522," EJC Supplements (2008) 6(12)141.
Ott et al., "CTLA-4 and PD-1/PD-L1 Blockade: New Immunotherapeutic Modalities with Durable Clinical Benefit in Melanoma Patients," Clin. Cancer Res. (Oct. 1, 2013) 19(19):5300-5309.
Pardoll et al., "The blockade of immune checkpoints in cancer immunotherapy," Nat Rev Cancer (May 4, 2016) 12(4): 252-264.
Rhodes, John, "Section Review: Biologicals & Immunologicals: Therapeutic potential of Schiff base-forming drugs," Expert Opinion on Investigational Drugs (1996) vol. 5, Issue 3, pp. 257-268.
Rozali et al., "Programmed Death Ligand 2 in Cancer-Induced Immune Suppression," Clinical and Developmental Immunology (2012) Article ID 656340, pp. 1-8.
Stenehjem et al., "PDI/PDLI inhibitors for the treatment of advanced urothelial bladder cancer," OncoTargets and Therapy (2018) 11:5973-5989.
Topalian et al., "Safety, Activity, and Immune Correlates of Anti-PD-1 Antibody in Cancer," N Engl J Med. (Jun. 28, 2012) 366(26):2443-2454.
Wang, Y. et al, "Structures of a diverse set of colchicine binding site inhibitors in complex with tubulin provide a rationale for drug discovery." FEBS Journal (2016) 283, 102-111.
Yeh et al., "A Phase 1 Trial Combining Plinabulin and Nivolumab for Metastatic Squamous NSCLC," International Association for the Study of Lung Cancer, Journal of Thoracic Oncology (Sep. 6, 2015) Abstract 602, p. 2.01-087.
Zheng, Lei, "Does vaccine-primed pancreatic cancer offer better candidates for immune-based therapies?" Immunotherapy (2014) 6(10):1017-1020.
Partial European Search Report dated Dec. 6, 2018 for EP 16 824 996.9.
Colombian Office Action dated Jul. 25, 2019.
Chinese OA dated Jun. 4, 2019.
3rd Party Opposition—Ecuador App. No. SENADI-2018-10481—published IP Gazette No. 638, Mar. 2018.

PLINABULIN COMPOSITIONS

INCORPORATION BY REFERENCE TO ANY PRIORITY APPLICATIONS

This application is a continuation of U.S. application Ser. No. 15/741,635 filed on Jan. 3, 2018, issued as U.S. Pat. No. 10,155,748 on Dec. 18, 2018, which is the U.S. National Phase of International Application No. PCT/US2016/041773 entitled PLINABULIN COMPOSITIONS, filed Jul. 11, 2016 and published on Jan. 19, 2017 as WO 2017/011399, which claims the benefit of U.S. Provisional Application No. 62/191,990, filed Jul. 13, 2015, the disclosure of which are incorporated herein by reference in their entireties.

BACKGROUND

Field

The present invention relates to the fields of chemistry and medicine. More particularly, the present invention relates to forms and compositions of plinabulin and their preparation.

Description of the Related Art

Plinabulin is a synthetic analog of diketopiperazine phenylahistin (halimide) discovered from marine and terrestrial *Aspergillus* sp. Plinabulin is structurally different from colchicine and its combretastatin-like analogs (eg, fosbretabulin) and binds at or near the colchicine binding site on tubulin monomers. Previous studies showed that plinabulin induced vascular endothelial cell tubulin depolymerization and monolayer permeability at low concentrations compared with colchicine and that it induced apoptosis in Jurkat leukemia cells. Studies of plinabulin as a single agent in patients with advanced malignancies (lung, prostate, and colon cancers) showed a favorable pharmacokinetic, pharmacodynamics, and safety profile.

SUMMARY OF THE INVENTION

Some embodiments relate to a plinabulin monohydrate.

Other embodiments relate to a plinabulin monohydrate in crystalline form.

Some embodiments relate to a plinabulin composition having more than about 90% by weight of plinabulin, based on the total weight of the composition.

Other embodiments relate to a plinabulin composition having more than about 99% by weight of plinabulin, based on the total weight of molecules in the composition other than water, dimethylformamide, ethanol, ethyl acetate, methanol, toluene, and acetic acid.

Some embodiments relate to a plinabulin composition, containing plinabulin and no more than about 1.9% by weight of impurities, based on the total weight of the composition other than water.

Other embodiments relate to a plinabulin composition, containing plinabulin and no more than about 1% by weight of impurities other than solvent molecules, based on the total weight of non-solvent molecules in the composition.

Some embodiments relate to a plinabulin composition having plinabulin and no more than about 1% by weight of impurities, based on a HPLC analysis.

Some embodiments relate to a process of preparing a plinabulin monohydrate or plinabulin composition.

DETAILED DESCRIPTION OF THE PREFERRED EMBODIMENT

Plinabulin, (3Z,6Z)-3-Benzylidene-6-{[5-(2-methyl-2-propanyl)-1H-imidazol-4-yl]methylene}-2,5-piperazin-edione, is a synthetic analog of the natural compound phenylahistin. Plinabulin can be readily prepared according to methods and procedures detailed in U.S. Pat. Nos. 7,064, 201 and 7,919,497, which are incorporated herein by reference in their entireties. Some embodiments relate to polymorphs and solvates (e.g., hydrates) of plinabulin and pharmaceutical compositions comprising the same. Some embodiments include methods of preparation and methods of treatment. In particular, some embodiments relate to a plinabulin monohydrate.

Plinabulin Monohydrate

Figure 1:
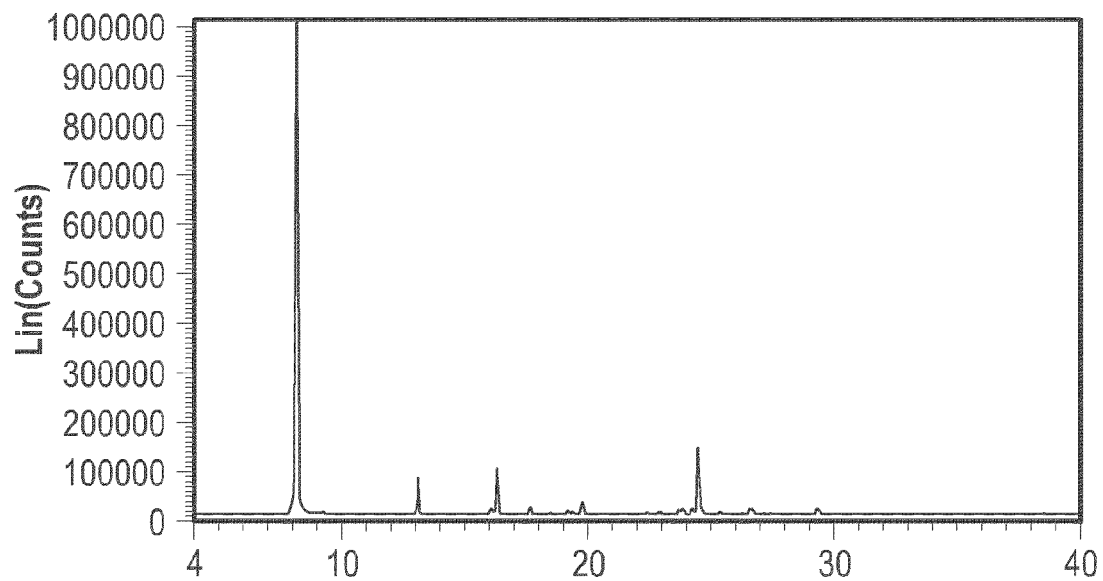
FIG. 1 is an X-ray powder diffraction (XRPD) pattern of the crystalline form of plinabulin monohydrate.

Plinabulin monohydrate (Form 1) is stable crystalline form of plinabulin. The X-ray powder diffraction (PXRD) pattern of plinabulin monohydrate (Form 1) is substantially the same as shown in FIG. 1, with corresponding tabulated peak data shown in Table 1.

TABLE 1

Peak Data of X-ray powder diffraction (PXRD) pattern of plinabulin monohydrate (Form 1)

| Angle (2-θ) | Intensity (%) | D value (angstrom) |
|---|---|---|
| 8.14 | 100.0 | 10.854 |
| 11.16 | 6.2 | 7.923 |
| 13.08 | 19.7 | 6.764 |
| 13.91 | 4.9 | 6.363 |
| 14.13 | 5.3 | 6.263 |
| 14.83 | 6.2 | 5.969 |
| 15.50 | 5.2 | 5.714 |
| 16.06 | 8.1 | 5.515 |
| 16.29 | 13.4 | 5.437 |
| 17.64 | 7.2 | 5.023 |
| 18.47 | 4.9 | 4.799 |
| 19.17 | 6.8 | 4.627 |
| 19.35 | 6.2 | 4.583 |
| 19.79 | 8.9 | 4.482 |
| 20.88 | 5.6 | 4.251 |
| 22.42 | 6.2 | 3.963 |
| 22.87 | 8.4 | 3.886 |
| 23.87 | 13.4 | 3.726 |
| 24.23 | 14.4 | 3.670 |
| 24.53 | 17.0 | 3.626 |
| 25.38 | 8.2 | 3.506 |
| 26.59 | 10.8 | 3.350 |
| 27.19 | 4.8 | 3.277 |
| 27.44 | 5.5 | 3.248 |
| 27.95 | 4.8 | 3.190 |
| 28.90 | 5.0 | 3.087 |
| 29.34 | 9.5 | 3.041 |

In some embodiments, the plinabulin monohydrate (Form 1) described herein includes a crystalline form exhibiting an X-ray powder diffraction pattern comprising at least three characteristic peaks selected from the group consisting of peaks at approximately 8.1°, 13.1°, 16.3°, 23.9°, 24.2°, 24.5°, and 26.6° 2θ. In some embodiments, the plinabulin monohydrate (Form 1) described herein includes a crystalline form exhibiting an X-ray powder diffraction pattern comprising at least peaks at approximately 8.1°, 13.1°, 16.3°, 23.9°, 24.2°, 24.5°, and 26.6° 2θ. In some embodiments, the plinabulin monohydrate (Form 1) described herein includes a crystalline form exhibiting an X-ray powder diffraction pattern comprising at least peaks at approximately 8.1°, 13.1°, 16.1°, 16.3°, 19.8°, 22.9°, 23.9°, 24.2°, 24.5°, 26.6°, and 29.3° 2θ.

As is well understood in the art, because of the experimental variability when X-ray diffraction patterns are measured on different instruments, the peak positions are assumed to be equal if the two theta (2θ) values agree to within 0.2° (i.e., ±0.2°). For example, the United States Pharmacopeia states that if the angular setting of the 10 strongest diffraction peaks agree to within ±0.2° with that of a reference material, and the relative intensities of the peaks do not vary by more than 20%, the identity is confirmed. Accordingly, peak positions within 0.2° of the positions recited herein are assumed to be identical. Unless otherwise indicated, all X-ray diffraction angles recited herein are based on a copper K-alpha source.

Figure 3A:
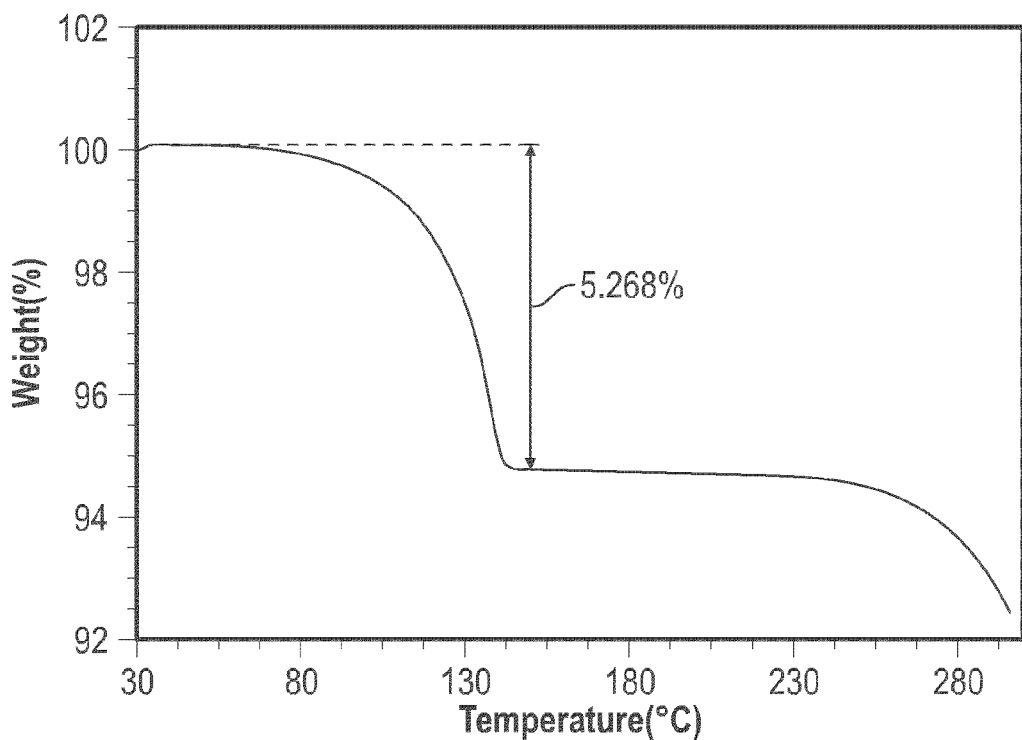
FIG. 3A shows the thermo gravimetric (TGA) of the crystalline form of plinabulin monohydrate (Form 1)
Figure 3B:
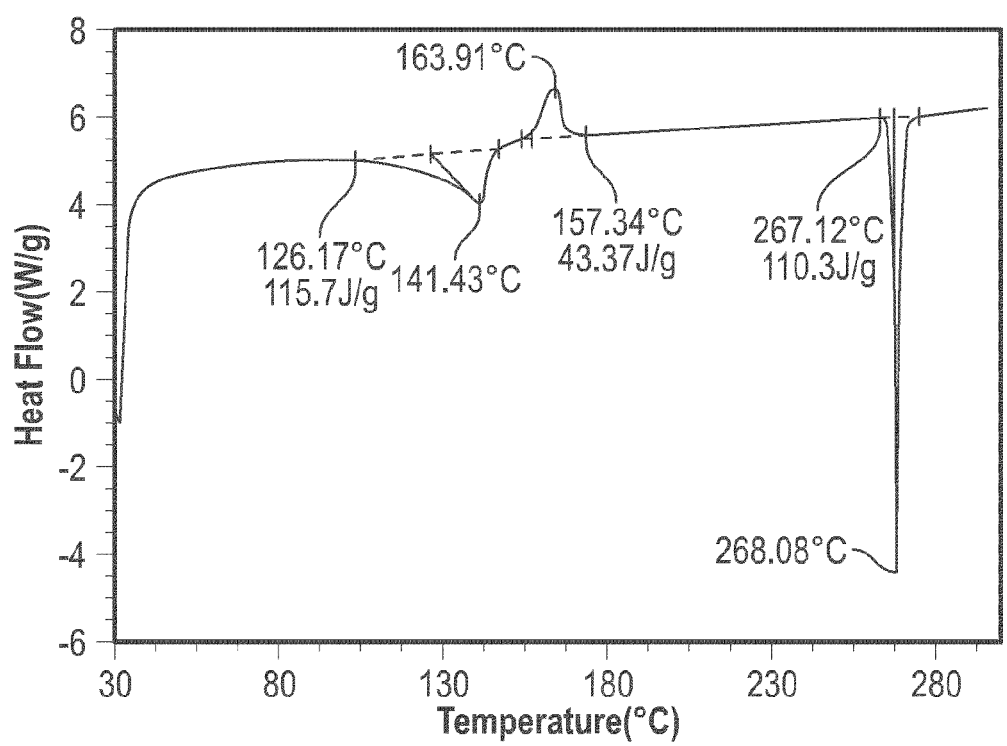
FIG. 3B shows the digital scanning calorimetry (DSC) analysis results of the crystalline form of plinabulin monohydrate (Form 1)

FIG. 3B shows digital scanning calorimetry (DSC) analysis results of the crystalline form of the plinabulin monohydrate (Form 1). As shown in FIG. 3B, the crystalline form of the plinabulin monohydrate (Form 1) has a melting point of about 267° C.; the crystalline form of the plinabulin monohydrate (Form 1) has a differential scanning calorimetry thermogram with endothermic peaks at about 141° C. and about 267° C.

The crystalline form of the plinabulin monohydrate (Form 1) is more stable than the other polymorph forms. The plinabulin monohydrate (Form 1) can remain stable during the DVS and drying tests as compared to other polymorph forms, which may show weight change and degradation during the tests.

Plinabulin Composition

Some embodiments relate to a plinabulin composition that includes more than about 50% by weight of the plinabulin monohydrate (Form 1) described herein, based on the total weight of the composition. In some embodiments, the plinabulin composition includes more than about 75% of the plinabulin monohydrate (Form 1) described herein. In some embodiments, the plinabulin composition includes more than about 90% of the plinabulin monohydrate described herein. In some embodiments, the plinabulin composition includes more than about 95% of the plinabulin monohydrate described herein. In some embodiments, the plinabulin composition includes more than about 98% of the plinabulin monohydrate described herein. In some embodiments, the plinabulin composition includes more than about 99% of the plinabulin monohydrate described herein. In some embodiments, the plinabulin composition includes the plinabulin monohydrate described herein in the range of about 50% to about 99%, about 60% to about 99%, about 70% to about 99%, about 80% to about 99%, about 90% to about 99%, about 95% to about 99%, or about 97.5% to about 99%, based on the total weight of the composition. The remaining portion of the plinabulin composition may be other forms of plinabulin and/or other chemical entities.

Some embodiments relate to a plinabulin composition with a high purity. In particularly, some embodiments relate to a plinabulin composition having more than about 90% by weight of plinabulin, based on the total weight of the composition. In some embodiments, the plinabulin composition includes more than about 92% of the plinabulin compound. In some embodiments, the plinabulin composition includes more than 80%, 85%, 86%, 87%, 88%, 89%, 90%, 91,%, 92%, 93%, 94%, 95%, 96%, 96.5%, 96%, 98%, 99%, or 99.6% of the plinabulin compound. In some embodiments, the plinabulin composition includes more than about 99% by weight of plinabulin, based on the total weight of non-solvent molecules in the composition. In some embodiments, the plinabulin composition includes more than about 96%, 97%, 98%, 99%, or 99.6% by weight of plinabulin, based on the total weight of non-solvent molecules in the composition. In some embodiments, the solvent can be water, dimethylformamide, ethanol, ethyl acetate, methanol, toluene, and acetic acid. In some embodiments, the plinabulin in the high-purity composition is present, at least in part, in plinabulin monohydrate as described above.

In some embodiments, the plinabulin composition includes more than about 99% by weight of a plinabulin, based on the total weight of molecules in the composition other than water, dimethylformamide, ethanol, ethyl acetate, methanol, toluene, and acetic acid. In some embodiments, the plinabulin composition includes more than about 80%, 85%, 86%, 87%, 88%, 89%, 90%, 91,%, 92%, 93%, 94%, 95%, 96%, 96.5%, 96%, 98%, 99%, or 99.6% by weight of a plinabulin, based on the total weight of molecules in the composition other than water, dimethylformamide, ethanol, ethyl acetate, methanol, toluene, and acetic acid. In some embodiments, the plinabulin in the composition is present, at least in part, in plinabulin monohydrate as described above.

In some embodiments, the plinabulin composition includes more than about 99% by weight of a plinabulin, based on a HPLC analysis. In some embodiments, the plinabulin composition includes more than about 80%, 85%, 86%, 87%, 88%, 89%, 90%, 91,%, 92%, 93%, 94%, 95%, 96%, 96.5%, 96%, 98%, 99%, or 99.6% by weight of a plinabulin, based on a HPLC analysis. In some embodiments, the plinabulin in the composition is present, at least in part, in plinabulin monohydrate as described above.

Some embodiments relate to a plinabulin composition with low levels of impurities. The term "impurity" as used herein refers to one or more components of the composition that is different from plinabulin and water. In some embodiments, the impurity can include one or more chemical compounds introduced during the synthesis of plinabulin. In some embodiments, the impurity can include dimethylformamide, ethanol, ethyl acetate, methanol, toluene, acetic acid, and other residual solvent.

In some embodiments, the plinabulin composition includes no more than about 1% by weight of impurities, based on the total weight of the composition. In some embodiments, the plinabulin composition includes no more than about 15%, 14%, 13%, 12%, 11%, 10%, 9%, 8%, 7%, 6%, 5%, 4%, 3%, 2%, 1%, 0.97%, 0.9%, 0.8%, 0.6%, 0.4% or 0.2% by weight of impurities, based on the total weight of the composition. In some embodiments, the plinabulin composition includes no more than about 1% by weight of impurities, based on the total weight of non-solvent molecules in the composition. In some embodiments, the plinabulin composition includes no more than about 15%, 14%, 13%, 12%, 11%, 10%, 9%, 8%, 7%, 6%, 5%, 4%, 3%, 2%, 1%, 0.97%, 0.9%, 0.8%, 0.6%, 0.4% or 0.2% by weight of impurities, based on the total weight of non-solvent molecules in the composition.

In some embodiments, the plinabulin composition includes no more than about 1.9% by weight of impurities, based on the total weight of the composition other than water. In some embodiments, the plinabulin composition includes no more than about 15%, 14%, 13%, 12%, 11%, 10%, 9%, 8%, 7%, 6%, 5%, 4%, 3%, 2%, 1%, 0.97%, 0.9%, 0.8%, 0.6%, 0.4% or 0.2% by weight of impurities, based on the total weight of the composition other than water. In some embodiments, the plinabulin composition includes no more than about 1% by weight of impurities, based on the total weight of non-solvent molecules in the composition other than water. In some embodiments, the plinabulin composition includes no more than about 15%, 14%, 13%, 12%, 11%, 10%, 9%, 8%, 7%, 6%, 5%, 4%, 3%, 2%, 1%, 0.97%, 0.9%, 0.8%, 0.6%, 0.4% or 0.2% by weight of impurities, based on the total weight of non-solvent molecules in the composition other than water.

In some embodiments, the plinabulin composition includes no more than about more than about 0.9% by weight of impurities other than dimethylformamide, ethanol, ethyl acetate, methanol, toluene, and acetic acid, based on the total weight of molecules in the composition other than water, dimethylformamide, ethanol, ethyl acetate, methanol, toluene, and acetic acid. In some embodiments, the plinabulin composition includes no more than about more than about 5%, 4%, 3%, 2%, 1%, 0.97%, 0.9%, 0.8%, 0.6%, 0.4% or 0.2% by weight of impurities other than dimethylformamide, ethanol, ethyl acetate, methanol, toluene, and acetic acid, based on the total weight of molecules in the composition other than water, dimethylformamide, ethanol, ethyl acetate, methanol, toluene, and acetic acid.

In some embodiments, the plinabulin composition includes no more than about more than about 1% by weight of impurities, based on a HPLC analysis. In some embodiments, the plinabulin composition includes no more than about more than about 5%, 4%, 3%, 2%, 1%, 0.97%, 0.9%, 0.8%, 0.6%, 0.4% or 0.2% by weight of impurities, based on a HPLC analysis.

Method of Preparation

Some embodiments relate to a process of preparing the plinabulin monohydrate or the plinabulin composition described herein, the method including: combining plinabulin and a first solvent system to form a first mixture, heating the first mixture to a temperature in the range of about 50° C. to 90° C., and cooling the first mixture to form a first precipitate.

In some embodiments, the process further includes filtering prior to cooling the first mixture. In some embodiments, the process further includes adding water to the first mixture prior to heating.

In some embodiments, the process described herein further includes filtering the first precipitate. In some embodiments, the process described herein further includes washing the first precipitate.

In some embodiments, the first solvent system can be water, alcohol, or a mixture of water and alcohol.

In some embodiments, the alcohol is selected from methanol, ethanol, isopropyl alcohol, tert-butyl alcohol and n-butyl alcohol; or mixture thereof.

In some embodiments, the alcohol is ethanol.

In some embodiments, heating the first mixture comprises refluxing the first mixture.

In some embodiments, the first mixture is heated to about 70° C. to 78° C. In some embodiments, the first mixture is heated to about 60° C. to 90° C. In some embodiments, the first mixture is heated to about 60° C. to 80° C. In some embodiments, the first mixture is heated to the boiling point of ethanol.

In some embodiments, the process described herein further includes maintaining the first mixture at a refluxing temperature for about 1 hour prior to cooling the first mixture.

In some embodiments, heating the first mixture includes heating the first mixture to at least 65° C., and wherein cooling the first mixture includes cooling the first mixture to about 50° C. to 60° C.

In some embodiments, the cooling of the first mixture includes adding water to the first mixture to produce the first precipitate.

In some embodiments, the cooling of the first mixture includes stirring the first mixture for at least 4 hours.

In some embodiments, the process described herein further includes analyzing the first precipitate to determine the plinabulin composition in the first precipitate.

In some embodiments, the process described herein further includes combining the first precipitate and a second solvent to form a second mixture and heating the second mixture to a temperature in the range of about 50° C. to 90°

C.; cooling the second mixture to form a second precipitate; and filtering the second precipitate and washing the second precipitate.

In some embodiments, the second solvent is water, alcohol, or a mixture of water and alcohol.

In some embodiments, the alcohol is selected from methanol, ethanol, isopropyl alcohol, tert-butyl alcohol and n-butyl alcohol; or mixture thereof. In some embodiments, the alcohol is ethanol.

In some embodiments, heating the second mixture comprises refluxing the second mixture.

In some embodiments, the second mixture is heated to about 70° C. to 78° C.

In some embodiments, the process described herein includes maintaining the second mixture at a refluxing temperature for about 1 hour prior to cooling the second mixture.

In some embodiments, cooling the second mixture comprises cooling the first mixture to about 15° C. to 30° C.

In some embodiments, the cooling of the second mixture comprises adding water to the second mixture to produce the second precipitate.

In some embodiments, the cooling of the second mixture comprises stirring the second mixture for at least 4 hours.

In some embodiments, the first precipitate is washed with an alcohol and the washed alcohol is collected and added to the second mixture prior to the heating.

In some embodiments, the process described herein includes drying the second precipitate In some embodiments, the process described herein includes analyzing the second precipitate to determine the plinabulin composition in the second precipitate.

In some embodiments, the combining, cooling, and filtering steps are repeated one or more times based on the plinabulin composition in the second precipitate.

Some embodiments relate to a process of preparing the plinabulin monohydrate or the plinabulin composition, wherein the process includes mixing plinabulin, ethanol, and water to form a mixture. In some embodiments, the process includes the mixture.

In some embodiments, the volume ratio of the ethanol to water is about 95:5. In some embodiments, the volume ratio of the ethanol to water is about 85:15, 90:10, 95:5, 97.5:2.5, or 99:1. In some embodiments, the volume ratio of the ethanol to water is about 15, 16, 17, 18, 19, 20, 21, 22, 23, 24, or 25.

In some embodiments, the mixture of plinabulin and the solvent system is stirred for at least about 1, 2, 3, 4, 5, 6, 7, 8, 9, 10, 15, or 20 hours. In some embodiments, the mixture is stirred for at least 2 hours.

In some embodiments, the mixing or stirring is performed at a temperature in the range of about 10° C. to about 50° C.; about 20° C. to about 40° C.; about 25° C. to about 35° C., or about 28° C. to about 32° C. In some embodiments, the mixing of plinabulin, ethanol and water to form the mixture or stirring of the mixture is performed at about 20° C., 25° C., 30° C., 35° C., or 40° C.

Figure 29:
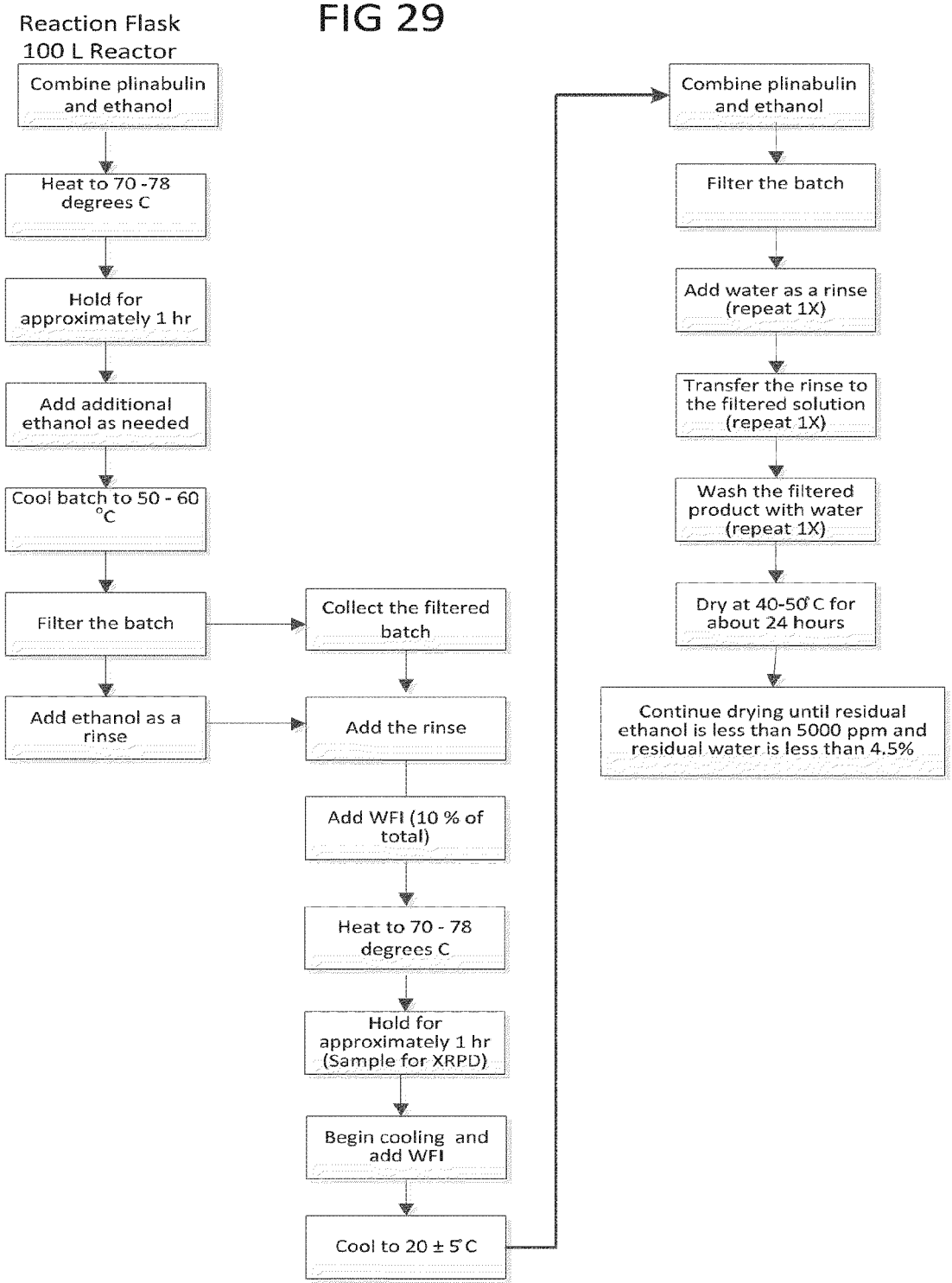
FIG. 29 is a flow diagram of preparing the plinabulin monohydrate composition.

FIG. 29 shows a block diagram of one method for producing the plinabulin monohydrate form composition. As shown in FIG. 29, the plinabulin compound and ethanol are added to a reaction flask, and the mixture is then heated to 70-78° C. and mixed at this temperature for about 1 hour. Additional ethanol can be added if needed. The flask is then cooled to about 50-60° C., the mixture is filtered, and ethanol is used as a rinse solvent. The filtered solution and the rinse solution are combined and water is added to about 10% of the combined solution. The solution is then heated to 70-78° C. and mixed at this temperature for about 1 hour. A sample is taken for XRPD analysis, and then the solution is cooled to 20±5° C. and added with water. The batch is filtered and water is used as a rinse. The filtered product is washed with water and then transferred to the drying trays to dry at 40-50° C. for about 24 hours or longer until it reaches the required ethanol and water content levels.

Plinabulin Crystalline Form 2

Some embodiments relate to a crystalline Form 2 of plinabulin and its process of preparation. While not being bound by any particular theory, it is believed that Form 2 is a plinabulin isopropyl alcohol (IPA)) solvate.

Figure 4:
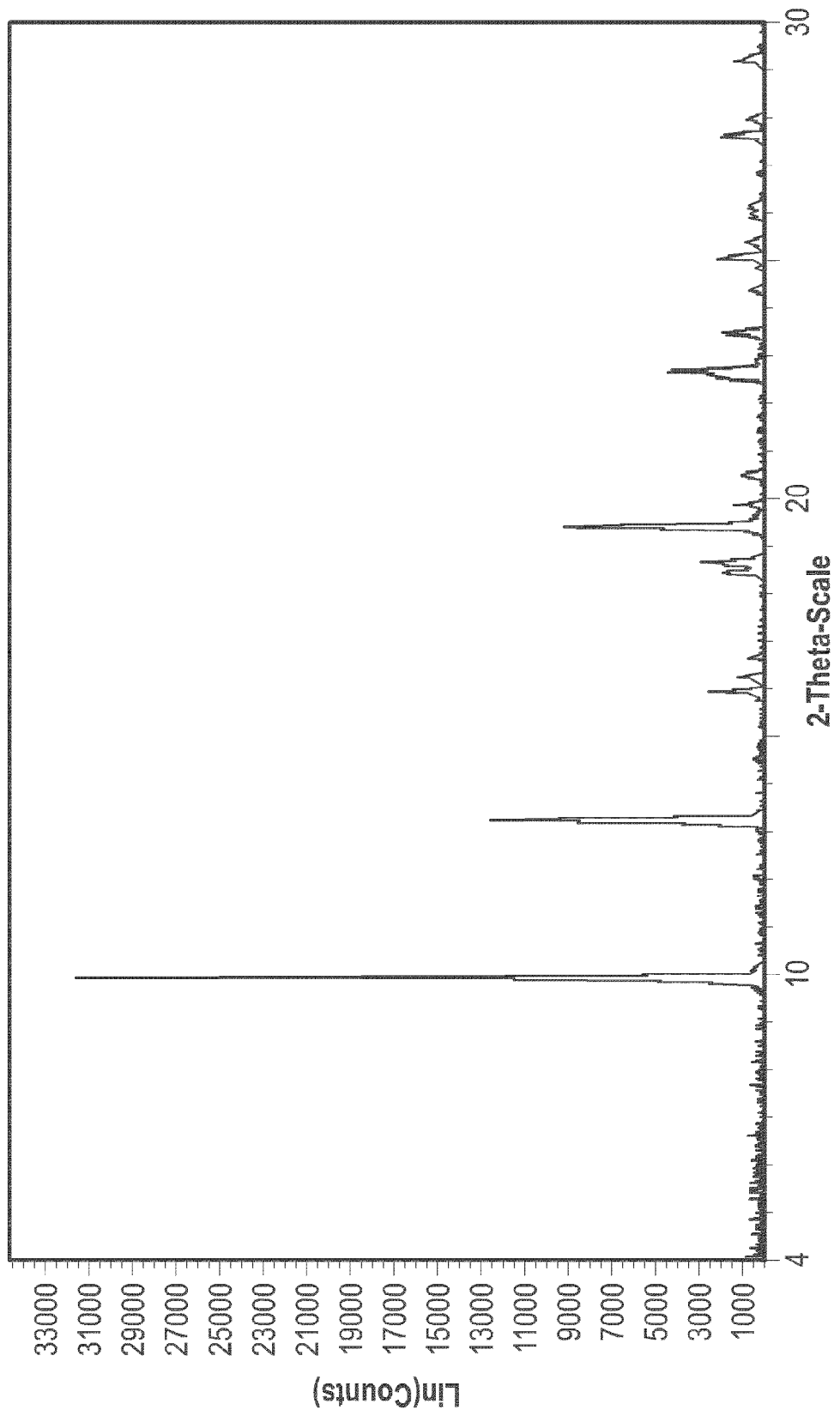
FIG. 4 is an XRPD pattern of the crystalline form 2.
Figure 5:
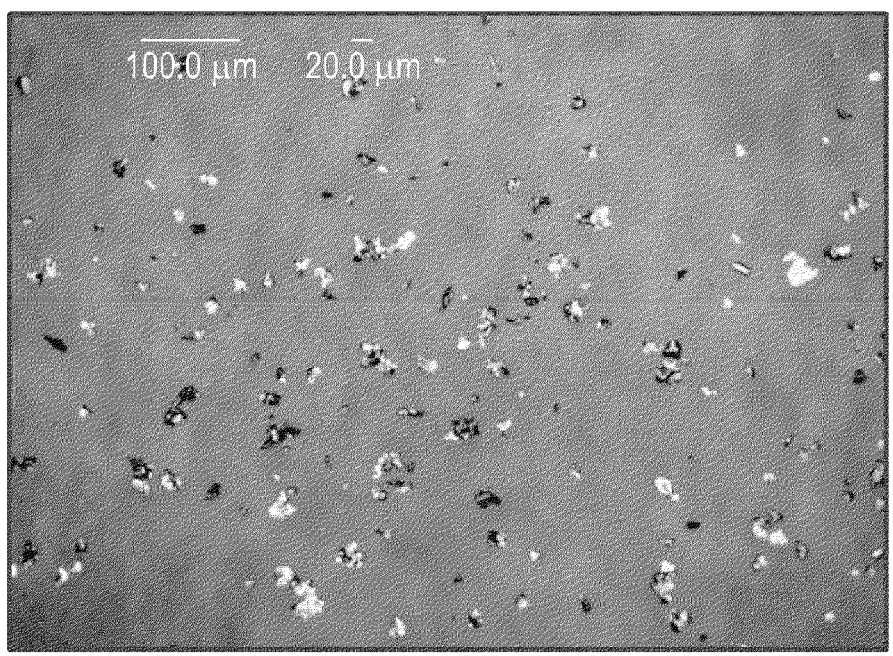
FIG. 5 shows a PLM image of a sample containing the crystalline form 2.

In some embodiments, crystalline Form 2 of plinabulin has substantially the same XRPD pattern as depicted in FIG. 4, with corresponding tabulated peak data shown in Table 2.

TABLE 2

Peak Data of PXRD pattern of crystalline Form 2

| Angle, 2θ | d spacing | Intensity, % |
|---|---|---|
| 9.93 | 8.90 | 100 |
| 13.25 | 6.68 | 39.6 |
| 15.96 | 5.55 | 7.9 |
| 16.28 | 5.44 | 3.7 |
| 16.69 | 5.31 | 2.2 |
| 18.47 | 4.80 | 5.5 |
| 18.68 | 4.75 | 9 |
| 19.45 | 4.56 | 28.9 |
| 19.90 | 4.46 | 4.2 |
| 20.53 | 4.32 | 3.1 |
| 22.71 | 3.91 | 14 |
| 23.51 | 3.78 | 6 |
| 24.44 | 3.64 | 2 |
| 25.12 | 3.54 | 6.7 |
| 25.45 | 3.50 | 2.6 |
| 26.06 | 3.42 | 1.4 |
| 26.19 | 3.40 | 1.9 |
| 27.69 | 3.22 | 5.9 |
| 28.04 | 3.18 | 2.3 |
| 29.27 | 3.05 | 4 |

Figure 6A:
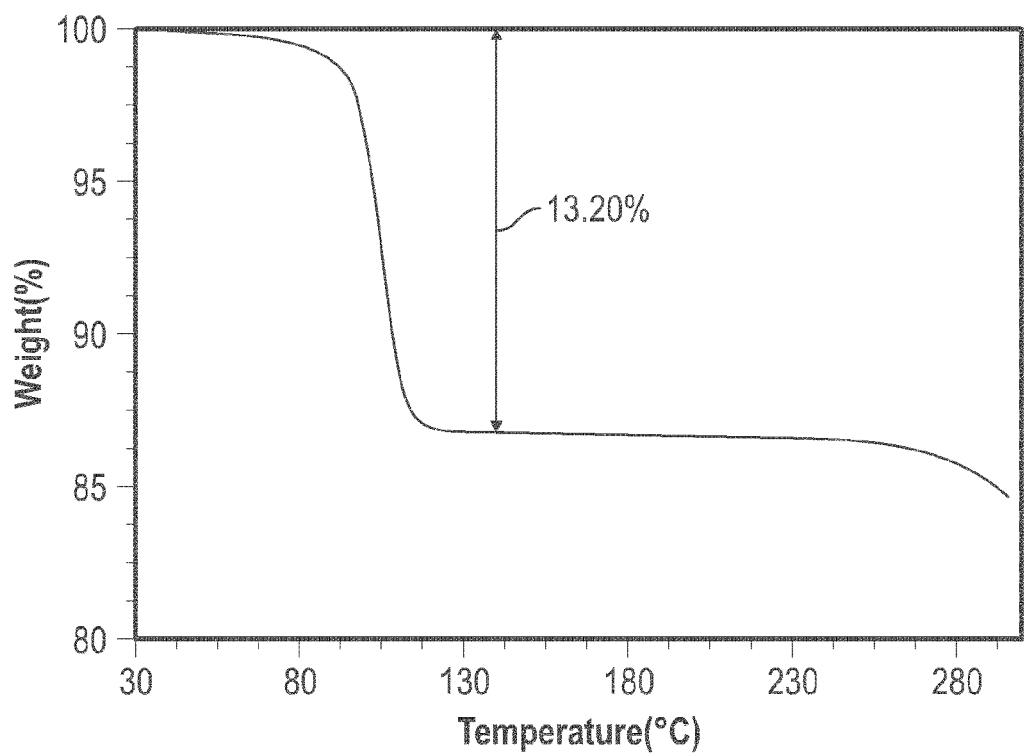
FIG. 6A shows the TGA analysis of the crystalline form 2 and FIG. 6B shows the DSC analysis results of the crystalline form 2.
Figure 6B:
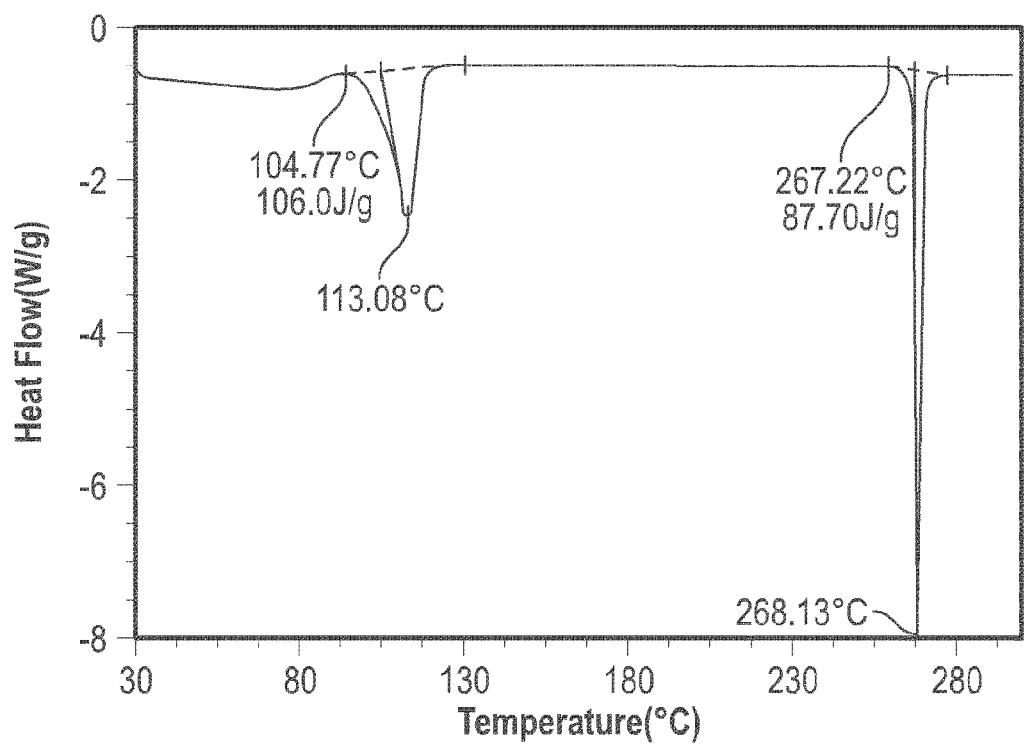

The crystalline Form 2 may further be characterized by a DSC thermogram substantially the same as that depicted in FIG. 6B. As shown in FIG. 6B, the crystalline Form 2 has a melting point of about 267° C.; the crystalline form of plinabulin Form 2 has a differential scanning calorimetry thermogram with endothermic peaks at about 113° C. and about 267° C.

Plinabulin Crystalline Form 3

Some embodiments relate to a crystalline Form 3 of plinabulin and its process of preparation. While not being bound by any particular theory, it is believed that Form 3 is an anhydrous form of plinabulin.

Figure 7:
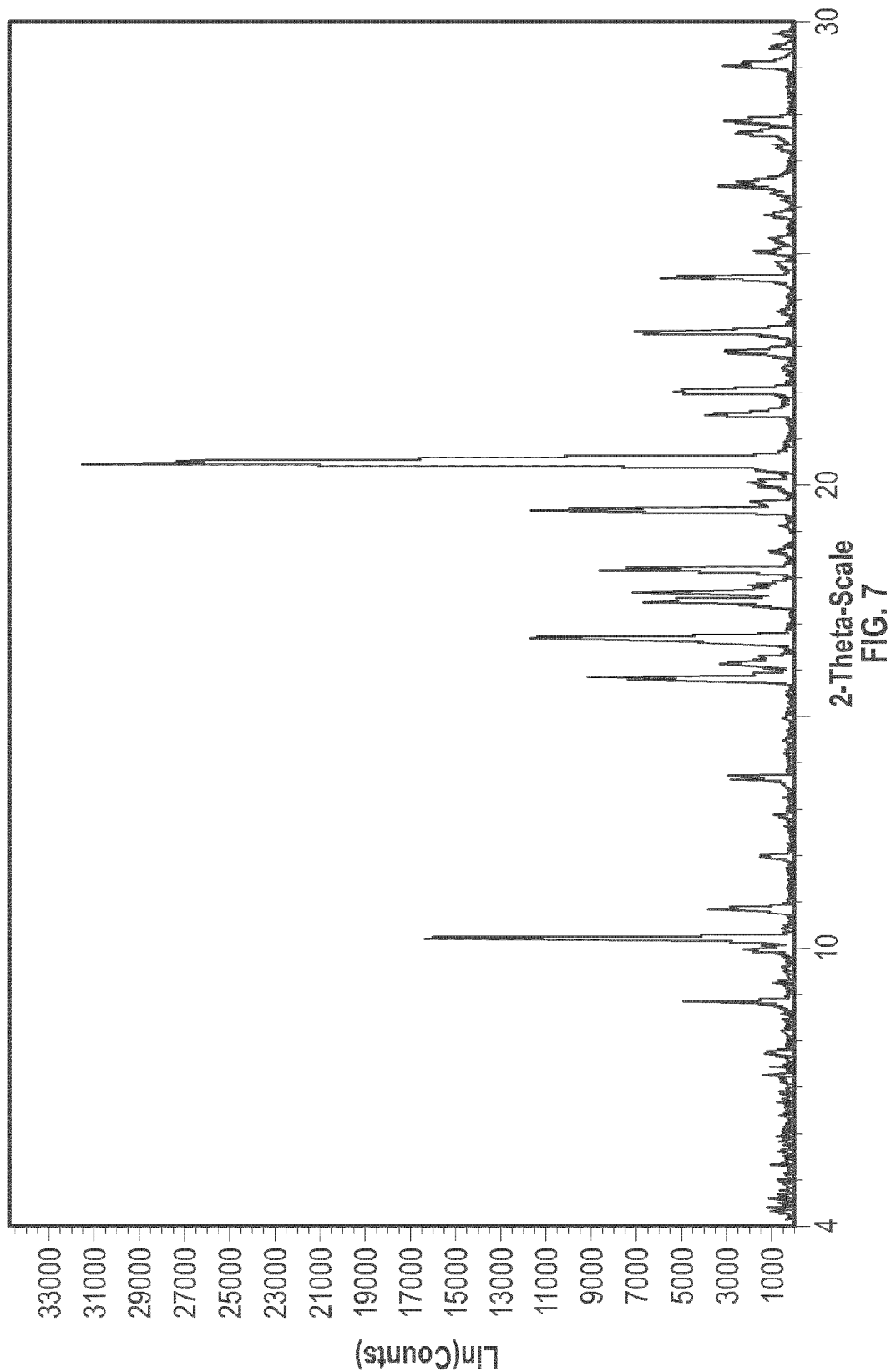
FIG. 7 is an XRPD pattern of the crystalline form 3.
Figure 8:
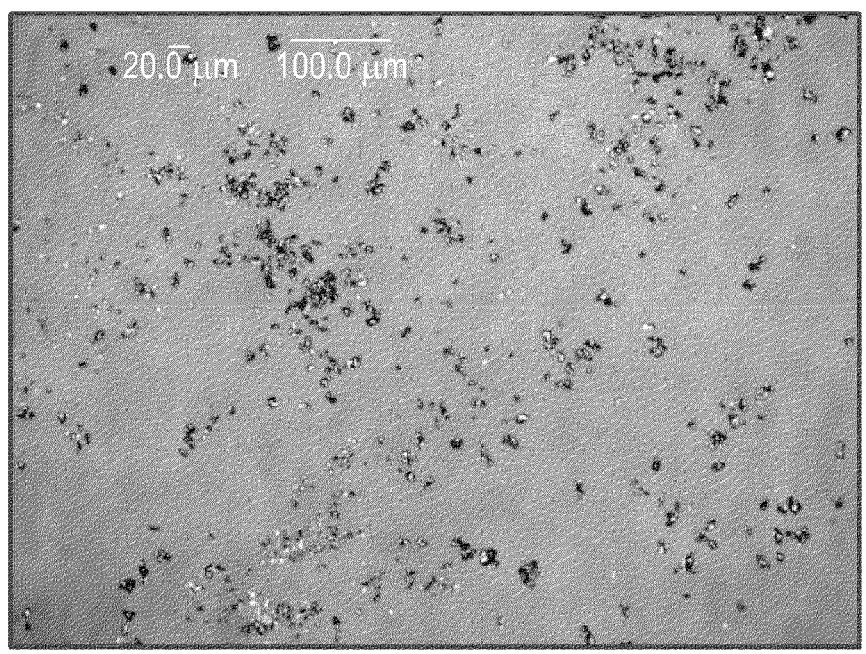
FIG. 8 shows a PLM image of a sample containing the crystalline form 3.

In some embodiments, crystalline Form 3 of plinabulin has substantially the same XRPD pattern as depicted in FIG. 7, with corresponding tabulated peak data shown in Table 3.

TABLE 3

Peak Data of PXRD pattern of crystalline Form 3

| Angle, 2θ | d spacing | Intensity, % |
|---|---|---|
| 7.75 | 11.40 | 4.3 |
| 8.84 | 9.99 | 17.8 |
| 9.97 | 8.86 | 7.9 |
| 10.21 | 8.66 | 59.2 |
| 10.86 | 8.14 | 13.9 |
| 11.99 | 7.38 | 5.2 |
| 12.87 | 6.87 | 3.2 |
| 13.69 | 6.46 | 10.3 |

TABLE 3-continued

Peak Data of PXRD pattern of crystalline Form 3

| Angle, 2θ | d spacing | Intensity, % |
|---|---|---|
| 15.87 | 5.58 | 32.7 |
| 16.15 | 5.48 | 11.7 |
| 16.71 | 5.30 | 41.9 |
| 17.54 | 5.05 | 23.9 |
| 17.73 | 5.00 | 25.8 |
| 17.86 | 4.96 | 8 |
| 18.19 | 4.87 | 31.4 |
| 18.59 | 4.77 | 3.9 |
| 19.15 | 4.63 | 2.3 |
| 19.50 | 4.55 | 42.4 |
| 20.06 | 4.42 | 7.5 |
| 20.52 | 4.32 | 100 |
| 21.58 | 4.11 | 14.2 |
| 22.08 | 4.02 | 19.4 |
| 22.92 | 3.88 | 10.9 |
| 23.35 | 3.81 | 25.3 |
| 24.54 | 3.63 | 20.3 |
| 24.80 | 3.59 | 2.8 |
| 25.10 | 3.55 | 6.2 |
| 25.34 | 3.51 | 3.8 |
| 25.89 | 3.44 | 4.5 |
| 26.53 | 3.36 | 10.2 |
| 27.35 | 3.26 | 2.7 |
| 27.65 | 3.22 | 9.4 |
| 27.93 | 3.19 | 11.2 |
| 29.13 | 3.06 | 11.3 |
| 29.54 | 3.02 | 3.1 |
| 29.81 | 29.81 | 29.81 |

Figure 9A:
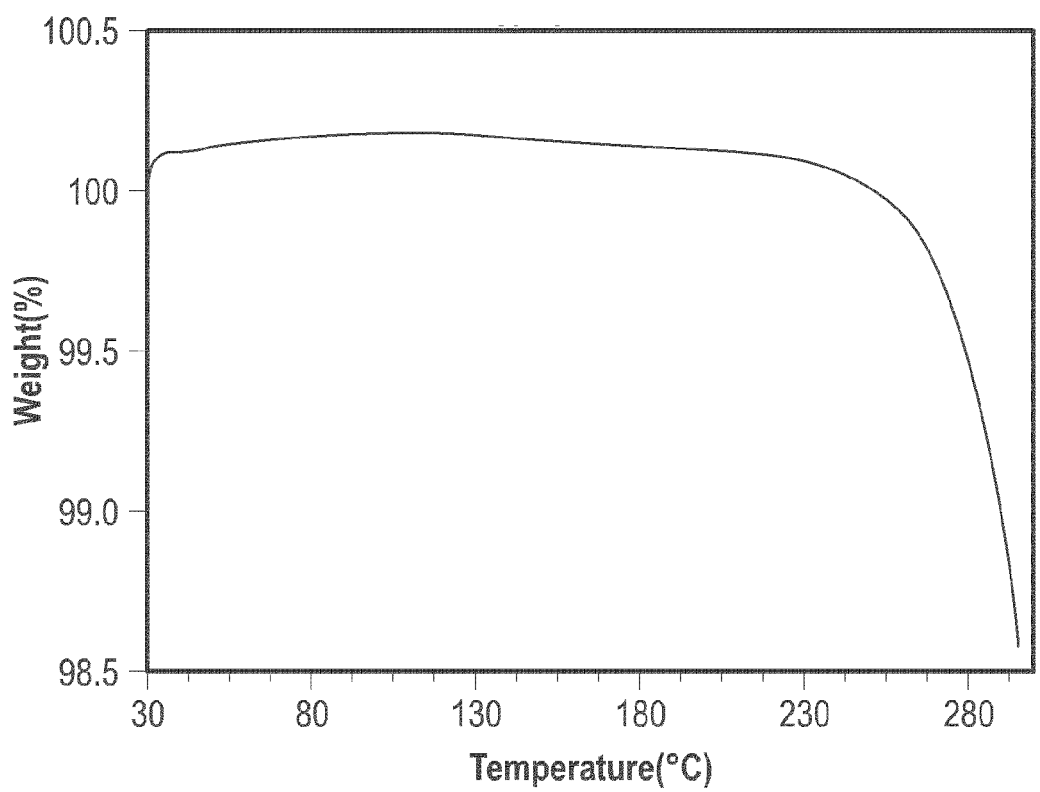
FIG. 9A shows the TGA analysis of the crystalline form 3.
Figure 9B:
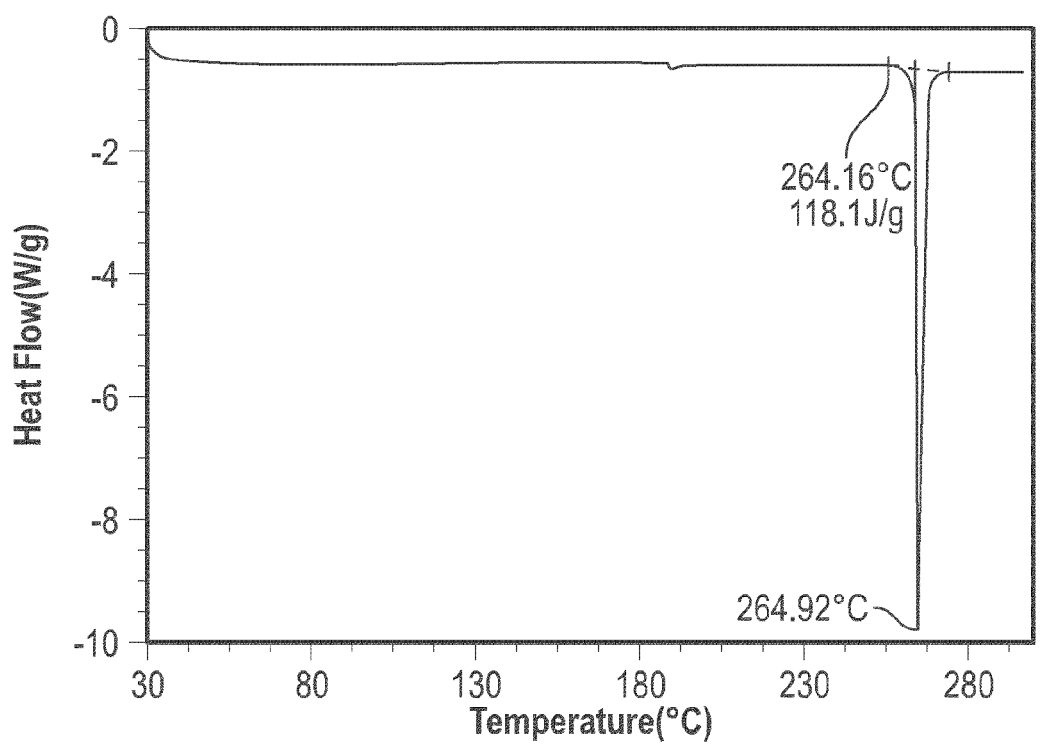
FIG. 9B shows the DSC analysis results of the crystalline form 3.

The crystalline Form 3 may further be characterized by a DSC thermogram substantially the same as that depicted in FIG. 9B. As shown in FIG. 9B, the crystalline Form 3 has a melting point of about 264° C.; the crystalline Form 3 has a differential scanning calorimetry thermogram with endothermic peak at about 264° C.

Plinabulin Crystalline Form 4

Some embodiments relate to a crystalline Form 4 of plinabulin and its process of preparation. While not being bound by any particular theory, it is believed that Form 4 is a plinabulin methanol solvate.

Figure 10:
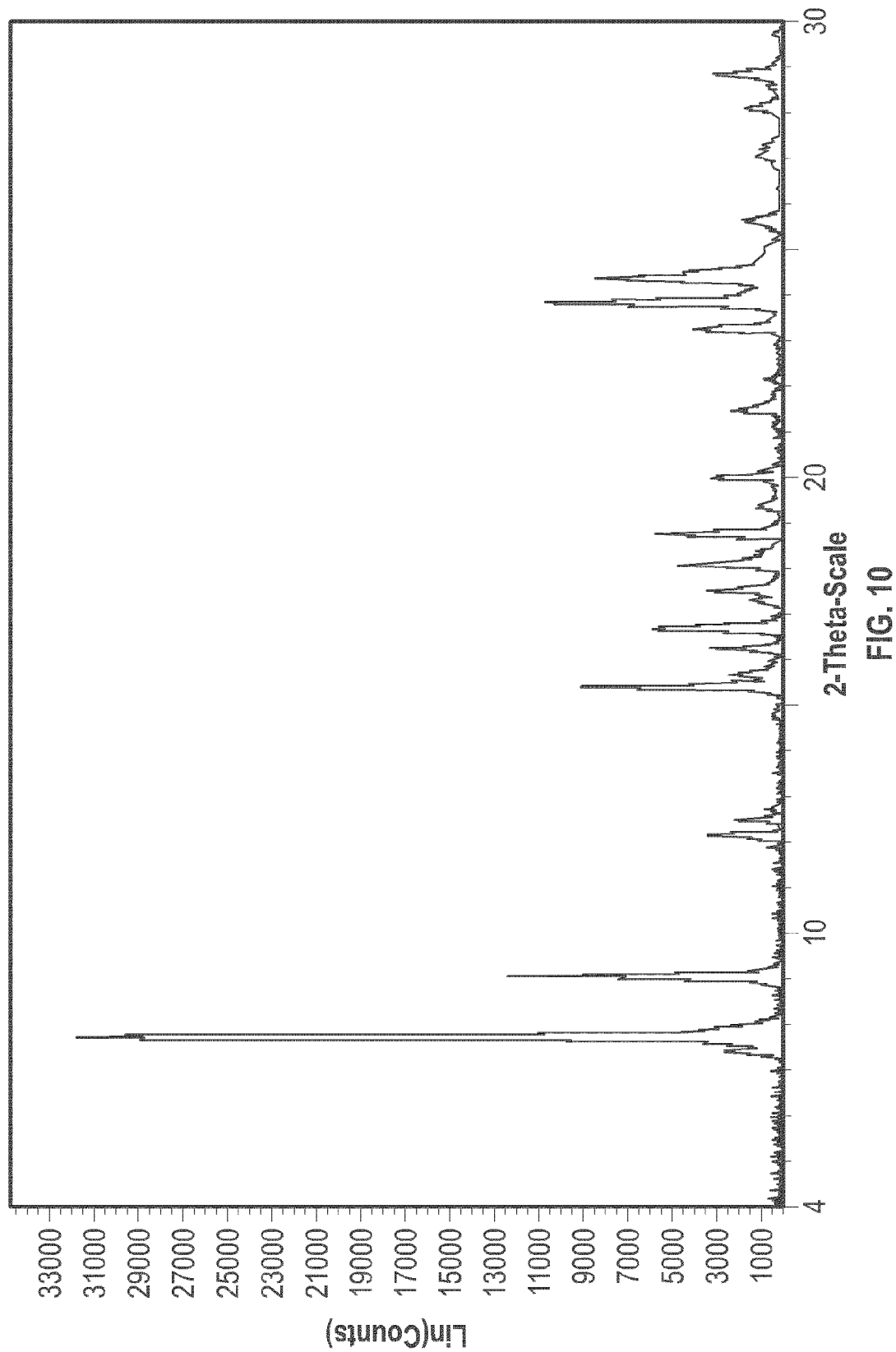
FIG. 10 is an XRPD pattern of the crystalline form 4.
Figure 11:
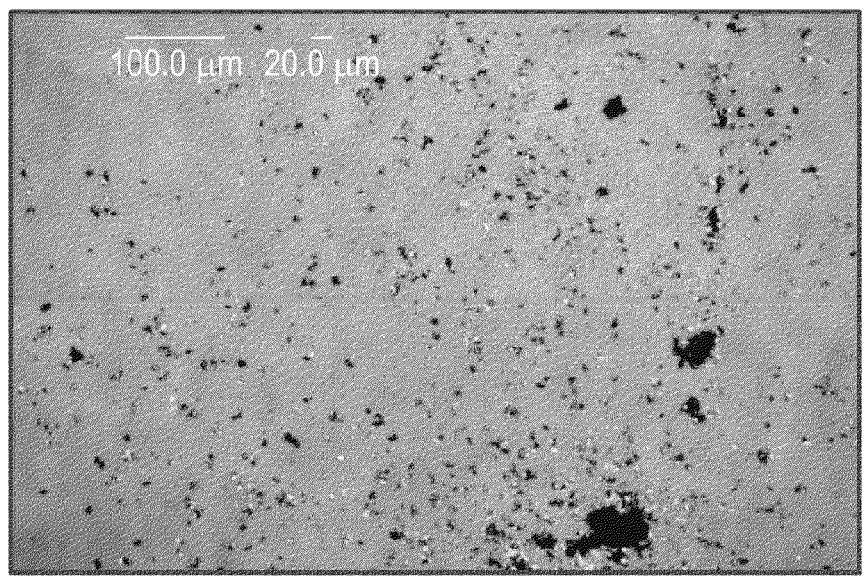
FIG. 11 shows a PLM image of a sample containing the crystalline form 4.

In some embodiments, crystalline Form 4 of plinabulin has substantially the same XRPD pattern as depicted in FIG. 10, with corresponding tabulated peak data shown in Table 4.

TABLE 4

Peak Data of PXRD pattern of crystalline Form 4

| Angle, 2θ | d spacing | Intensity, % |
|---|---|---|
| 7.41 | 11.93 | 7.9 |
| 7.71 | 11.45 | 100 |
| 9.06 | 9.76 | 38.6 |
| 12.16 | 7.28 | 10.2 |
| 12.50 | 7.07 | 5.6 |
| 12.74 | 6.94 | 2.2 |
| 15.44 | 5.73 | 28.2 |
| 15.70 | 5.64 | 7.2 |
| 16.27 | 5.44 | 10.1 |
| 16.72 | 5.30 | 17.4 |
| 17.33 | 5.11 | 4.6 |
| 17.56 | 5.05 | 10.5 |
| 18.13 | 4.89 | 14.6 |
| 18.79 | 4.72 | 17.5 |
| 19.39 | 4.57 | 3.5 |
| 20.03 | 4.43 | 9.6 |
| 21.53 | 4.12 | 7 |
| 23.32 | 3.81 | 12.4 |
| 23.90 | 3.72 | 33.5 |
| 24.42 | 3.64 | 26.2 |

TABLE 4-continued

Peak Data of PXRD pattern of crystalline Form 4

| Angle, 2θ | d spacing | Intensity, % |
|---|---|---|
| 25.69 | 3.47 | 5.3 |
| 27.08 | 3.29 | 3.3 |
| 28.15 | 3.17 | 4.4 |
| 28.90 | 3.09 | 9.6 |

Figure 12A:
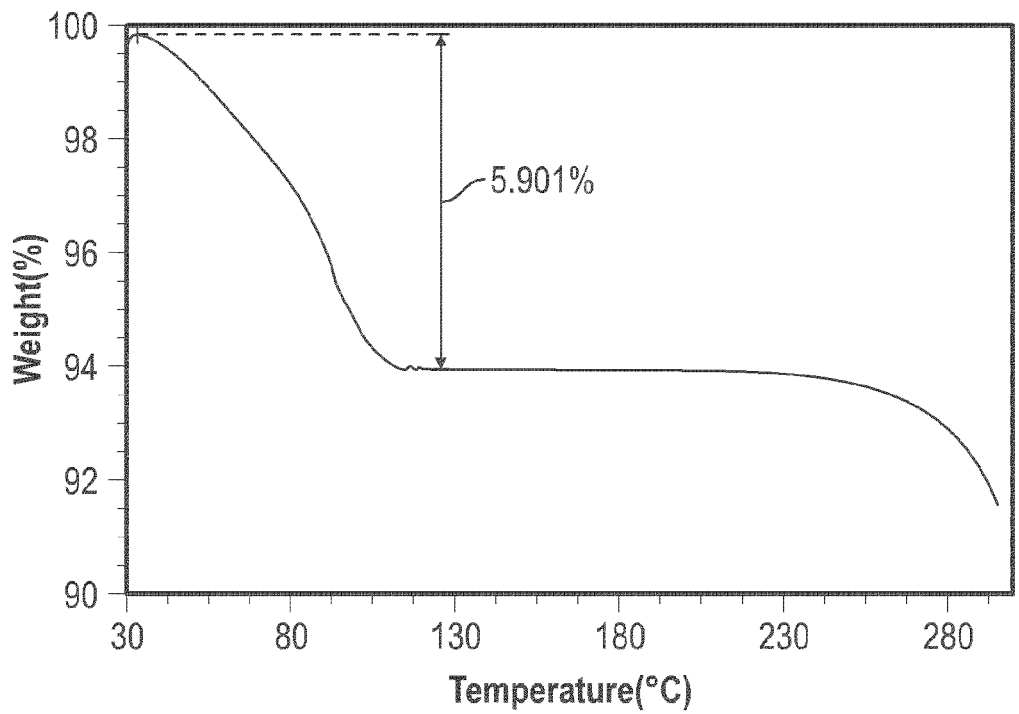
FIG. 12A shows the TGA analysis of the crystalline form 4.
Figure 12B:
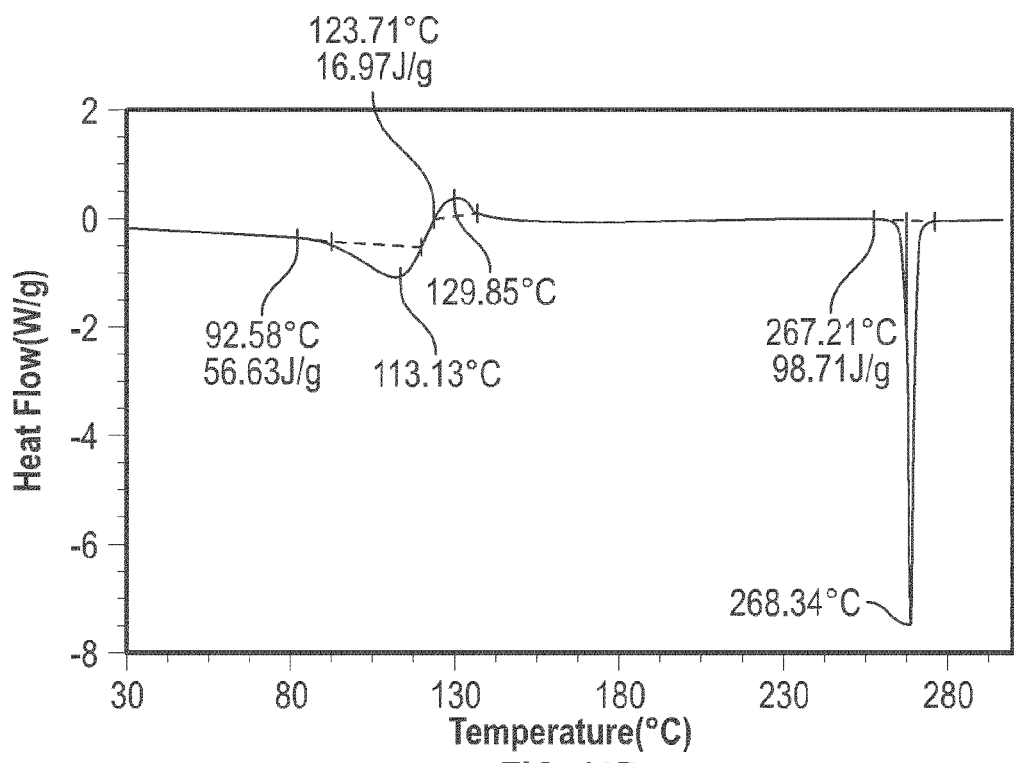
FIG. 12B shows the digital scanning calorimetry (DSC) analysis results of the crystalline form 4.

The crystalline Form 4 may further be characterized by a DSC thermogram substantially the same as that depicted in FIG. 12B. As shown in FIG. 12B, the crystalline Form 4 has a melting point of about 267° C.; the crystalline Form 4 has a differential scanning calorimetry thermogram with endothermic peaks at about 113° C. and at about 264° C.

Plinabulin Crystalline Form 5

Some embodiments relate to a crystalline Form 5 of plinabulin and its process of preparation.

Figure 13:
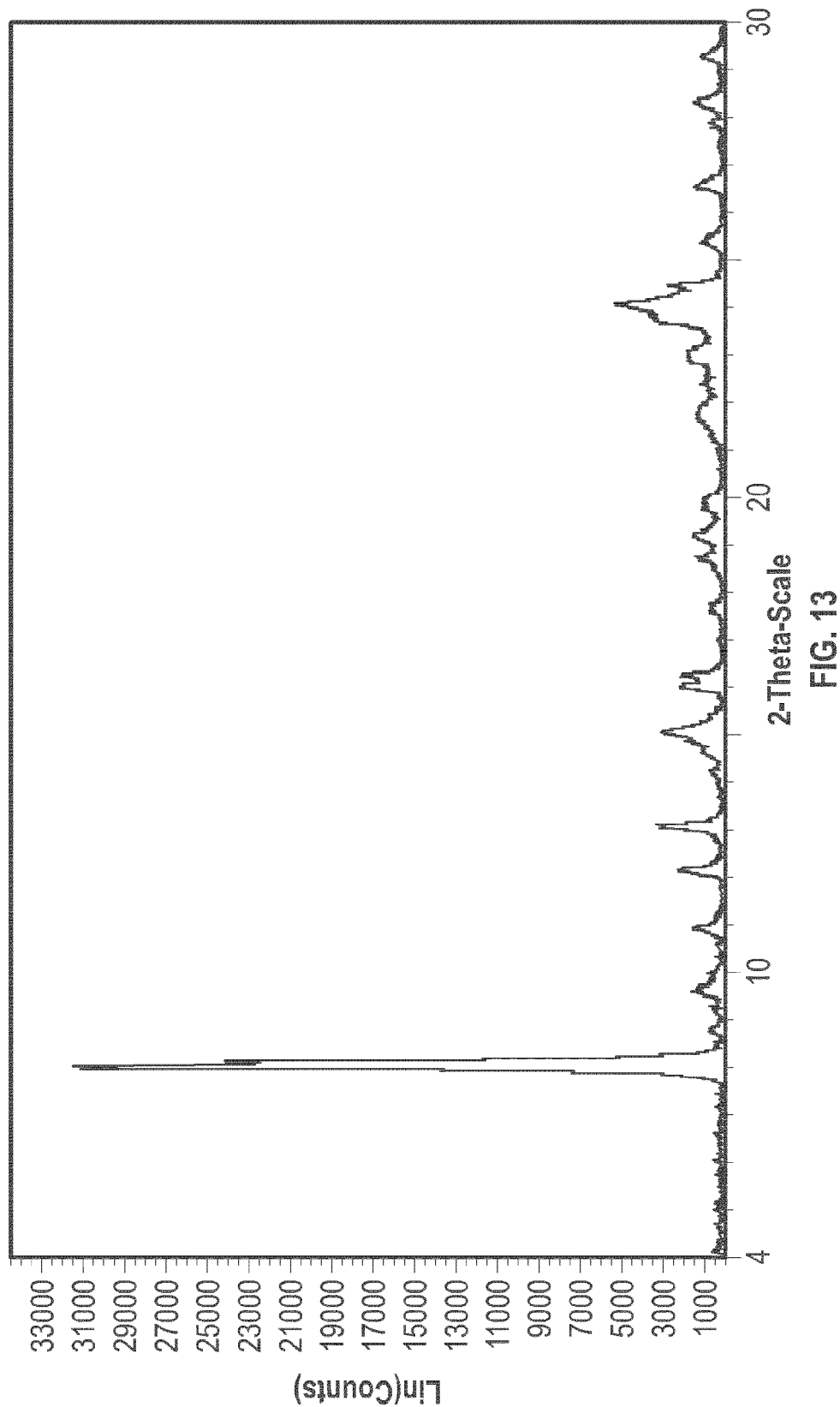
FIG. 13 is an XRPD pattern of the crystalline form 5.
Figure 14:
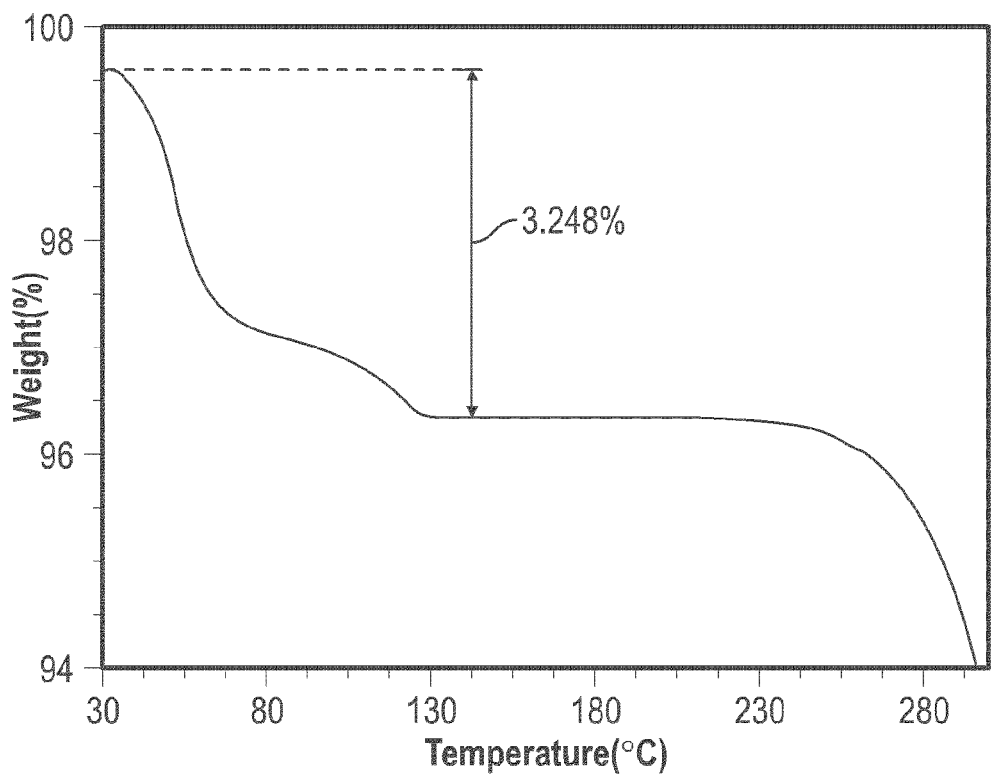
FIG. 14 shows the TGA analysis of the crystalline form 5

In some embodiments, crystalline Form 5 of plinabulin has substantially the same XRPD pattern as depicted in FIG. 13, with corresponding tabulated peak data shown in Table 5.

TABLE 5

Peak Data of PXRD pattern of crystalline Form 5

| Angle, 2θ | d spacing | Intensity, % |
|---|---|---|
| 8.04 | 10.99 | 100 |
| 8.79 | 10.06 | 2.2 |
| 9.64 | 9.17 | 4.2 |
| 10.94 | 8.08 | 5 |
| 12.15 | 7.28 | 7.2 |
| 13.09 | 6.76 | 10.9 |
| 15.07 | 5.87 | 9.5 |
| 16.04 | 5.52 | 6.9 |
| 16.25 | 5.45 | 6.9 |
| 17.67 | 5.01 | 2.2 |
| 18.76 | 4.73 | 4.4 |
| 19.20 | 4.62 | 4.8 |
| 19.81 | 4.48 | 3.6 |
| 21.84 | 4.07 | 4.1 |
| 23.06 | 3.85 | 6 |
| 23.87 | 3.72 | 11.8 |
| 24.10 | 3.69 | 17.1 |
| 24.49 | 3.63 | 8.8 |
| 25.43 | 3.50 | 3.8 |
| 26.60 | 3.35 | 4.5 |
| 27.91 | 3.19 | 2.6 |
| 28.36 | 3.14 | 4.9 |
| 29.36 | 3.04 | 3.5 |

Figure 15:
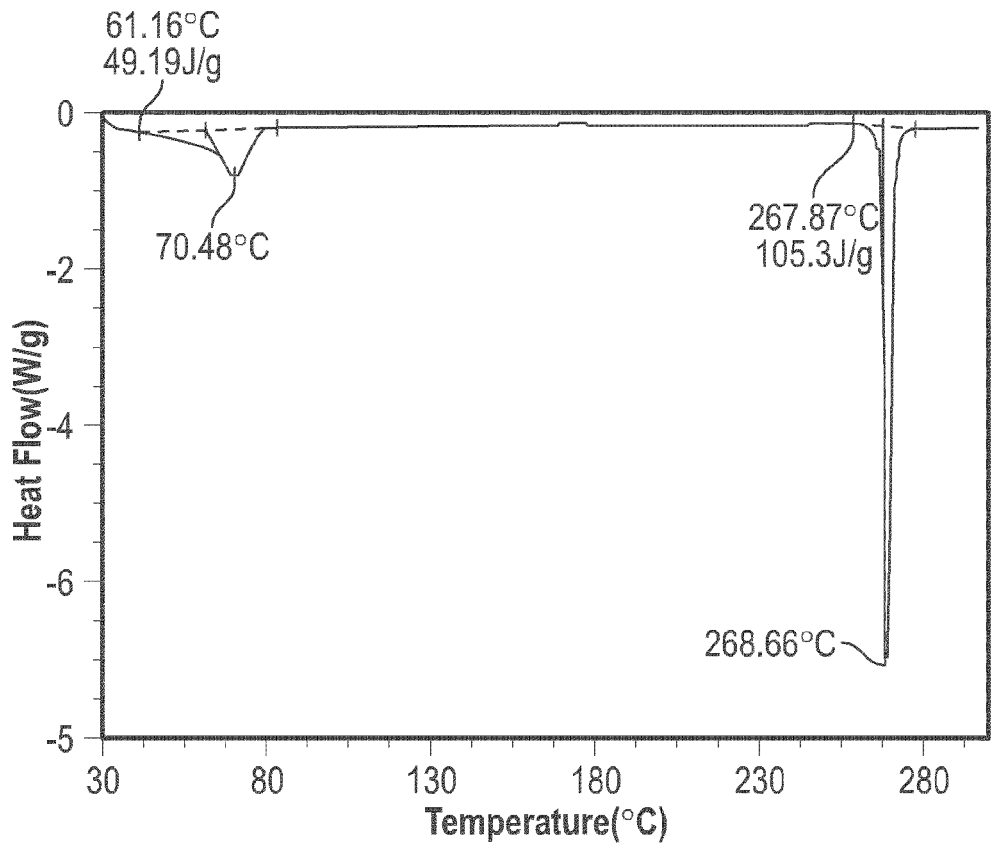
FIG. 15 shows the DSC analysis results of the crystalline form 5.

The crystalline Form 5 may further be characterized by a DSC thermogram substantially the same as that depicted in FIG. 15. As shown in FIG. 15, the crystalline Form 5 has a melting point of about 267° C.; the crystalline Form 5 has a differential scanning calorimetry thermogram with endothermic peaks at about 70° C. and at about 267° C.

Plinabulin Crystalline Form 6

Some embodiments relate to a crystalline Form 6 of plinabulin and its process of preparation.

Figure 16:
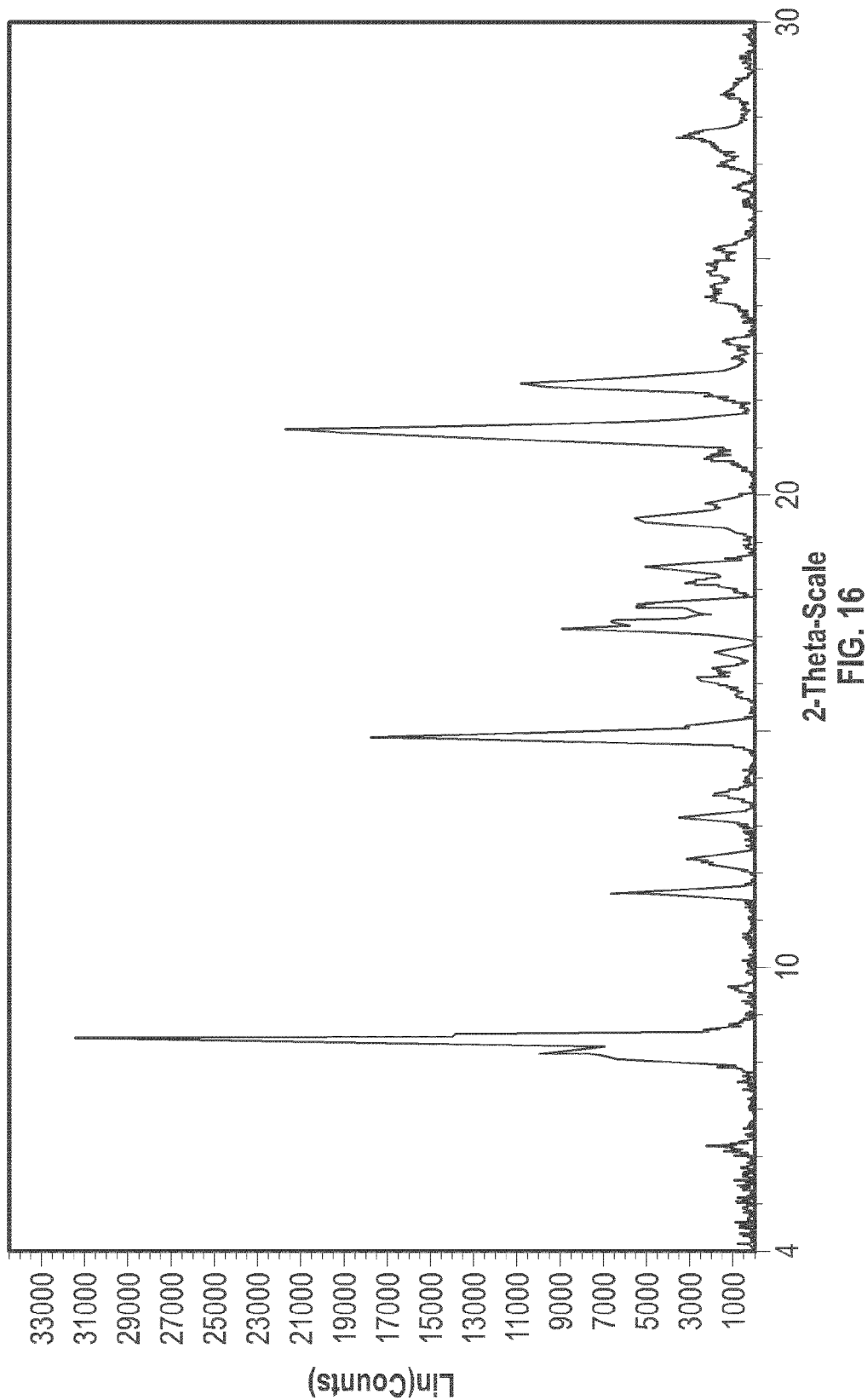
FIG. 16 is an XRPD pattern of the crystalline form 6.
Figure 17:
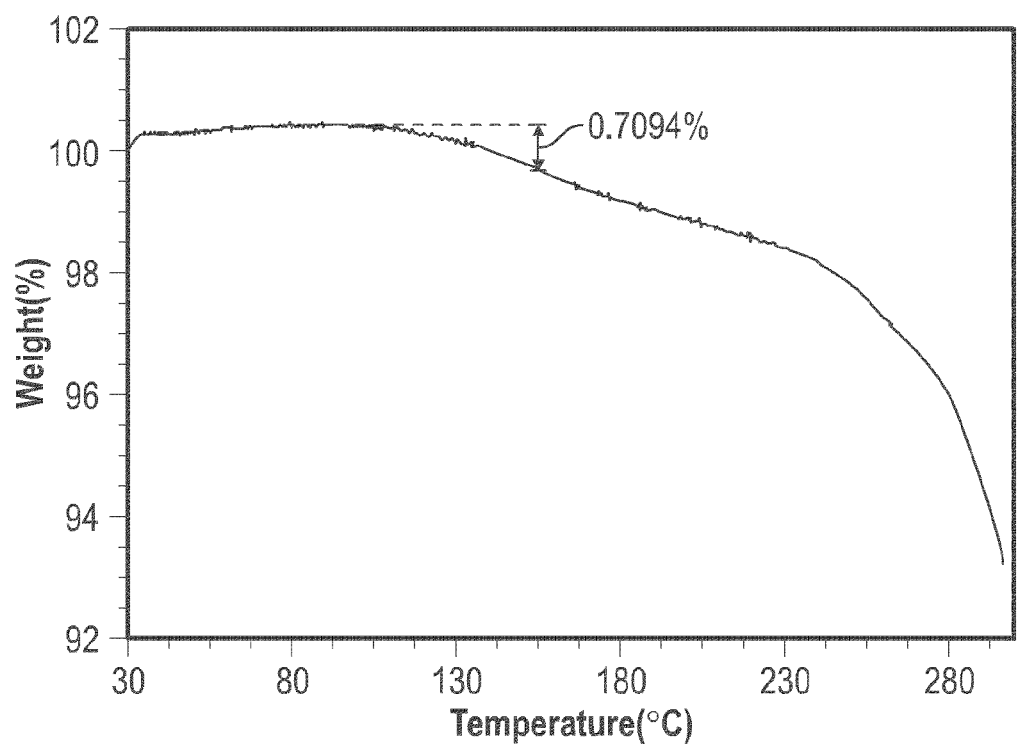
FIG. 17 shows the TGA analysis of the crystalline form 6

In some embodiments, crystalline Form 6 of plinabulin has substantially the same XRPD pattern as depicted in FIG. 16, with corresponding tabulated peak data shown in Table 6.

TABLE 6

Peak Data of PXRD pattern of crystalline Form 6

| Angle, 2θ | d spacing | Intensity, % |
|---|---|---|
| 6.18 | 14.28 | 8.6 |
| 8.21 | 10.77 | 32.1 |
| 8.49 | 10.41 | 100 |
| 9.56 | 9.25 | 3.8 |
| 11.59 | 7.63 | 21.4 |
| 12.32 | 7.18 | 9.9 |
| 13.20 | 6.70 | 11 |
| 13.69 | 6.46 | 6.6 |
| 14.90 | 5.94 | 57.4 |
| 16.08 | 5.51 | 8.1 |
| 16.68 | 5.31 | 5.7 |
| 17.20 | 5.15 | 27.9 |
| 17.33 | 5.11 | 21 |
| 17.68 | 5.01 | 17.4 |
| 18.19 | 4.87 | 10.5 |
| 18.50 | 4.79 | 16.6 |
| 19.53 | 4.54 | 18.6 |
| 20.84 | 4.26 | 7.1 |
| 21.40 | 4.15 | 69.3 |
| 22.40 | 3.97 | 34.7 |
| 23.30 | 3.81 | 4.9 |
| 24.28 | 3.66 | 8 |
| 24.76 | 3.59 | 6.9 |
| 25.25 | 3.52 | 6.2 |
| 26.57 | 3.35 | 3.2 |
| 27.05 | 3.29 | 5.4 |
| 27.68 | 3.22 | 10.2 |
| 28.55 | 3.12 | 4.9 |

Figure 18:
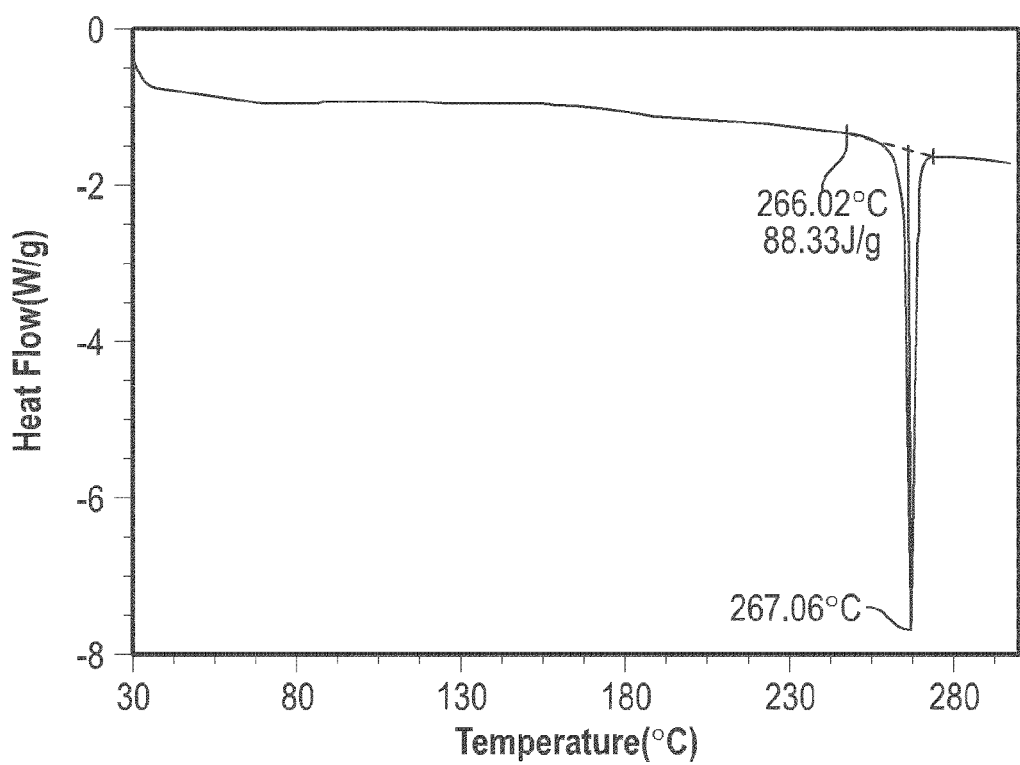
FIG. 18 shows the DSC analysis results of the crystalline form 6.

The crystalline Form 6 may further be characterized by a DSC thermogram substantially the same as that depicted in FIG. 18. As shown in FIG. 18, the crystalline Form 6 has a melting point of about 267° C.; the crystalline Form 6 has a differential scanning calorimetry thermogram with endothermic peak at about 267° C.

Plinabulin Crystalline Form 7

Some embodiments relate to a crystalline Form 7 of plinabulin and its process of preparation.

Figure 19:
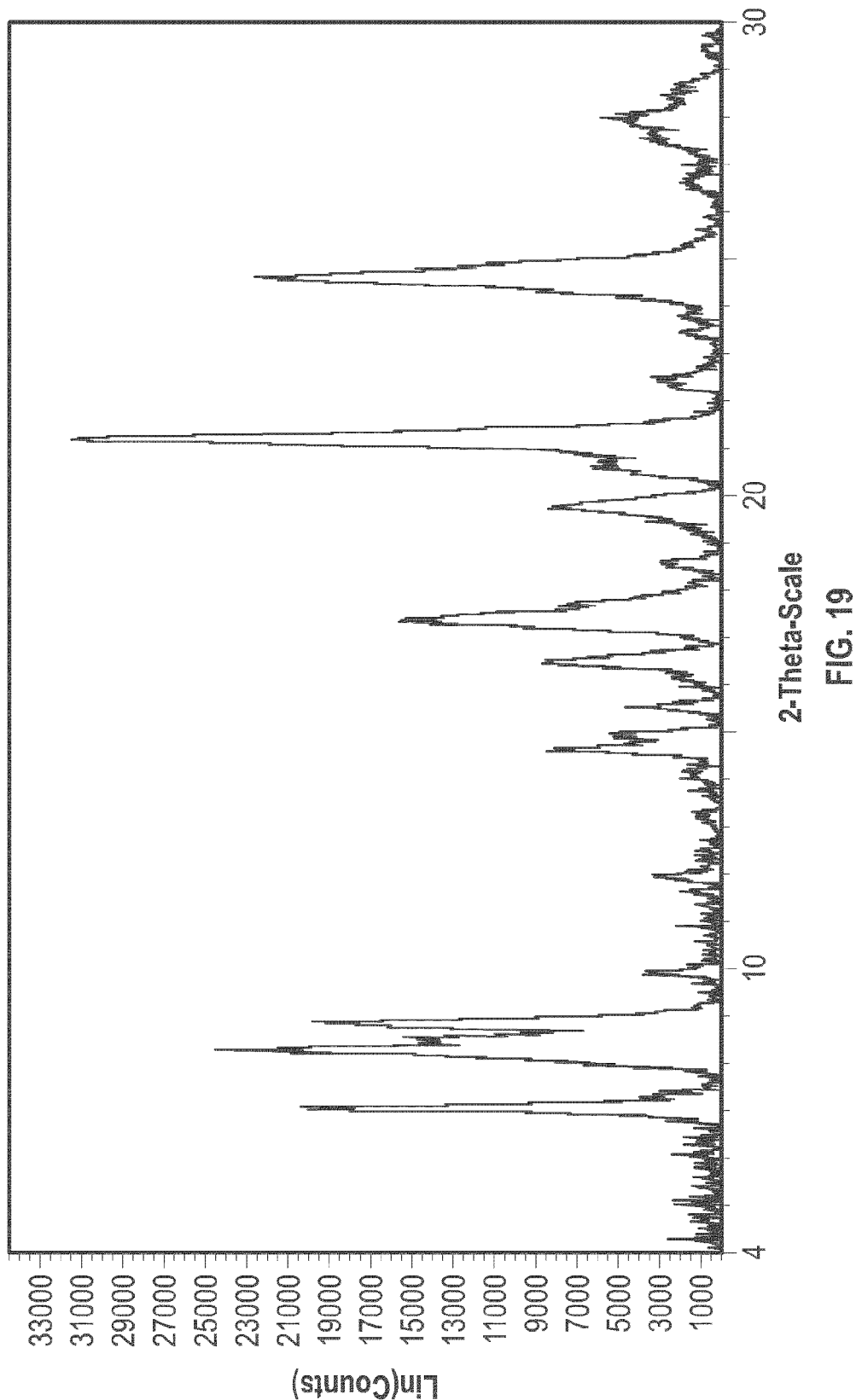
FIG. 19 is an XRPD pattern of the crystalline form 7.
Figure 20:
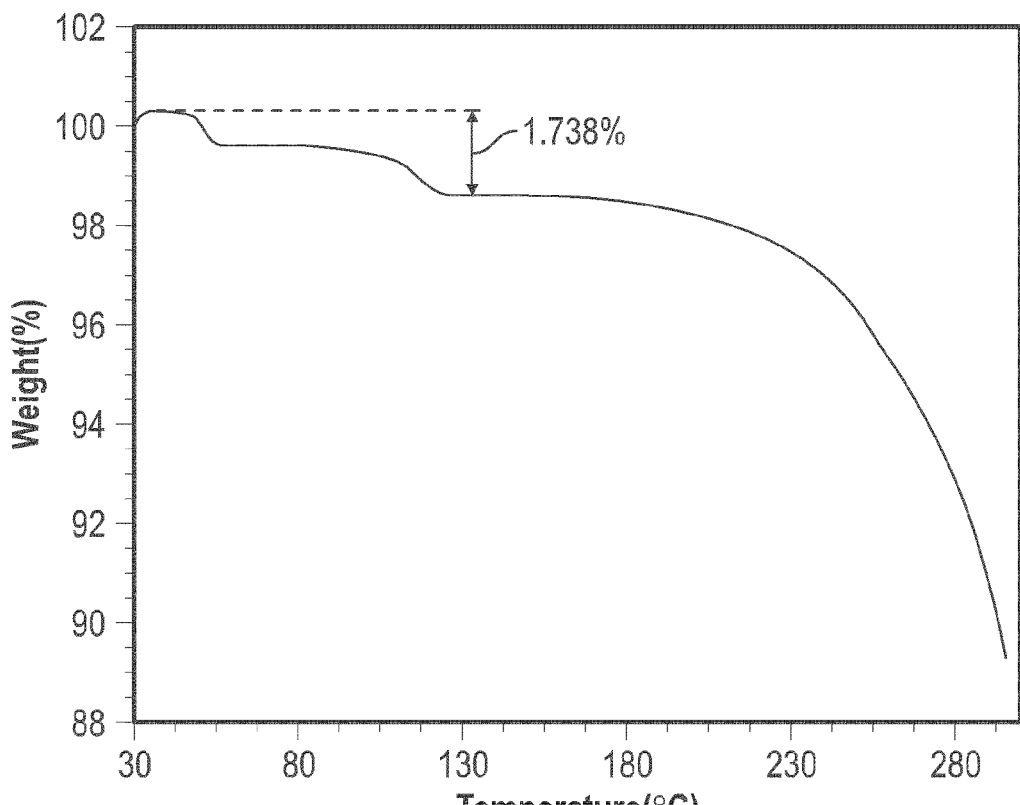
FIG. 20 shows the TGA of the crystalline form 7

In some embodiments, crystalline Form 7 of plinabulin has substantially the same XRPD pattern as depicted in FIG. 19, with corresponding tabulated peak data shown in Table 7.

TABLE 7

Peak Data of PXRD pattern of crystalline Form 7

| Angle, 2θ | d spacing | Intensity, % |
|---|---|---|
| 6.18 | 14.28 | 8.6 |
| 8.21 | 10.77 | 32.1 |
| 8.49 | 10.41 | 100 |
| 9.56 | 9.25 | 3.8 |
| 11.59 | 7.63 | 21.4 |
| 12.32 | 7.18 | 9.9 |
| 13.20 | 6.70 | 11 |
| 13.69 | 6.46 | 6.6 |
| 14.90 | 5.94 | 57.4 |
| 16.08 | 5.51 | 8.1 |
| 16.68 | 5.31 | 5.7 |
| 17.20 | 5.15 | 27.9 |
| 17.33 | 5.11 | 21 |
| 17.68 | 5.01 | 17.4 |
| 18.19 | 4.87 | 10.5 |
| 18.50 | 4.79 | 16.6 |
| 19.53 | 4.54 | 18.6 |
| 20.84 | 4.26 | 7.1 |
| 21.40 | 4.15 | 69.3 |
| 22.40 | 3.97 | 34.7 |
| 23.30 | 3.81 | 4.9 |
| 24.28 | 3.66 | 8 |
| 24.76 | 3.59 | 6.9 |
| 25.25 | 3.52 | 6.2 |
| 26.57 | 3.35 | 3.2 |
| 27.05 | 3.29 | 5.4 |
| 27.68 | 3.22 | 10.2 |
| 28.55 | 3.12 | 4.9 |

Figure 21:
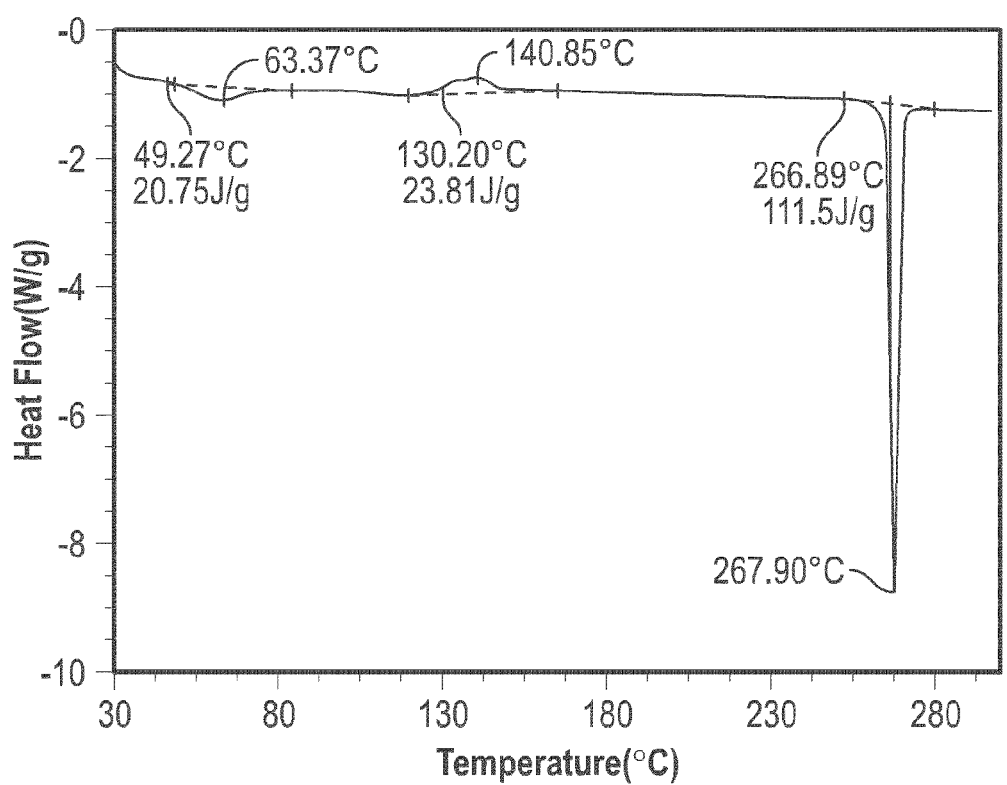
FIG. 21 shows the DSC analysis results of the crystalline form 7.

The crystalline Form 7 may further be characterized by a DSC thermogram substantially the same as that depicted in FIG. 21. As shown in FIG. 21, the crystalline Form 7 has a melting point of about 267° C.; the crystalline Form 7 has a differential scanning calorimetry thermogram with endothermic peaks at about 63° C. and at about 267° C.

Plinabulin Crystalline Form 8

Some embodiments relate to a crystalline Form 8 of plinabulin and its process of preparation.

Figure 22:
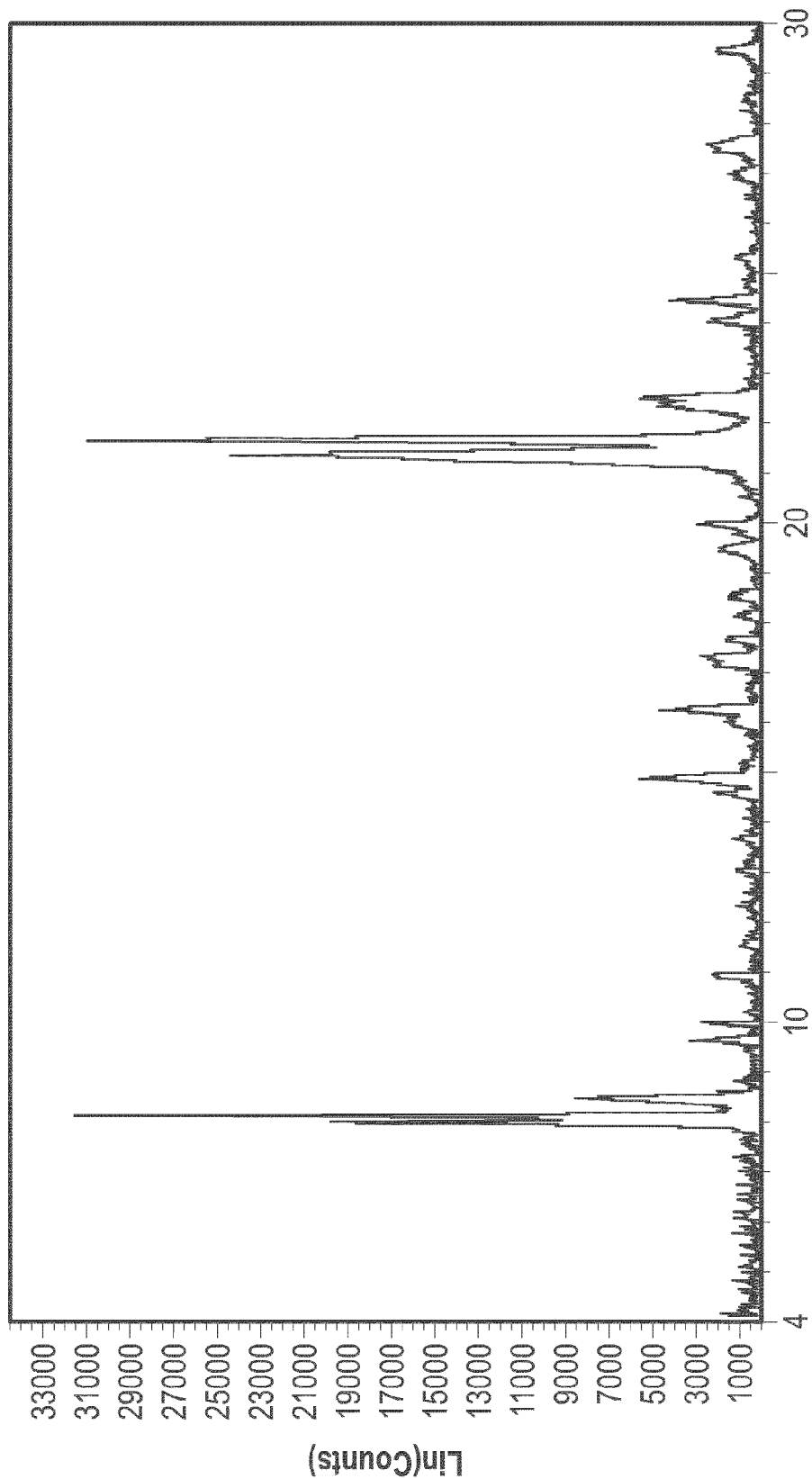
FIG. 22 is an XRPD pattern of the crystalline form 8.
Figure 23:
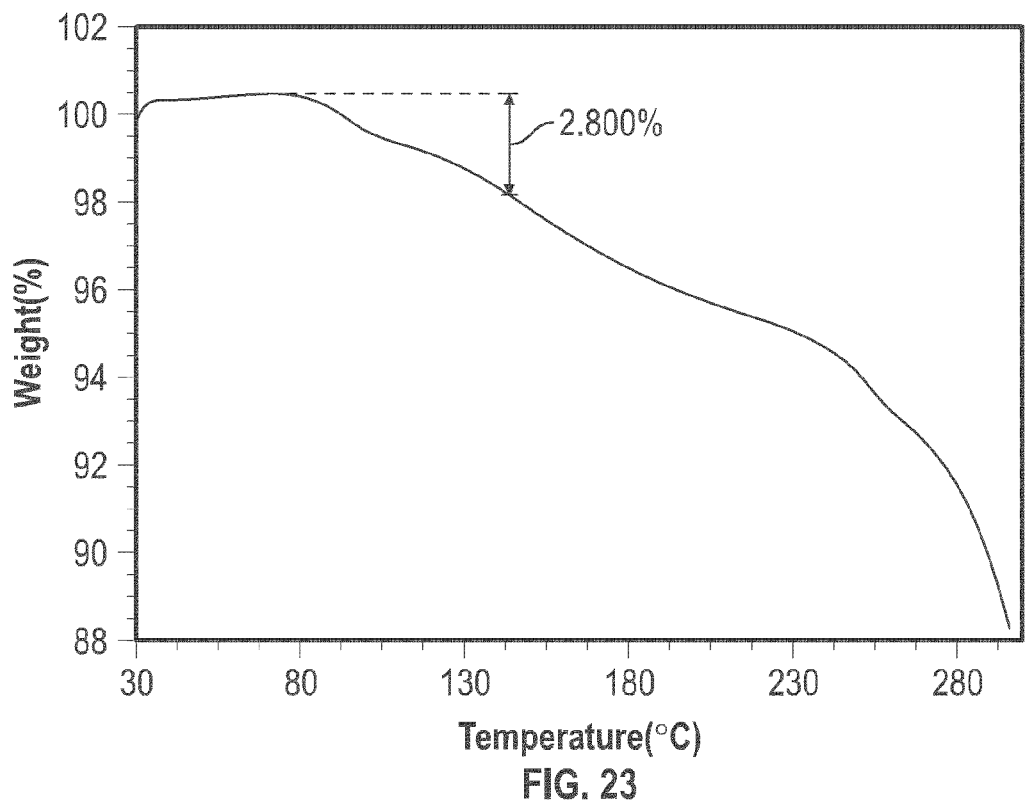
FIG. 23 shows the TGA of the crystalline form 8.

In some embodiments, crystalline Form 8 of plinabulin has substantially the same XRPD pattern as depicted in FIG. 22, with corresponding tabulated peak data shown in Table 8.

TABLE 8

Peak Data of PXRD pattern of crystalline Form 8

| Angle, 2θ | d spacing | Intensity, % |
|---|---|---|
| 6.18 | 14.28 | 8.6 |
| 8.21 | 10.77 | 32.1 |
| 8.49 | 10.41 | 100 |
| 9.56 | 9.25 | 3.8 |
| 11.59 | 7.63 | 21.4 |
| 12.32 | 7.18 | 9.9 |
| 13.20 | 6.70 | 11 |
| 13.69 | 6.46 | 6.6 |
| 14.90 | 5.94 | 57.4 |
| 16.08 | 5.51 | 8.1 |
| 16.68 | 5.31 | 5.7 |
| 17.20 | 5.15 | 27.9 |
| 17.33 | 5.11 | 21 |
| 17.68 | 5.01 | 17.4 |
| 18.19 | 4.87 | 10.5 |
| 18.50 | 4.79 | 16.6 |
| 19.53 | 4.54 | 18.6 |
| 20.84 | 4.26 | 7.1 |
| 21.40 | 4.15 | 69.3 |
| 22.40 | 3.97 | 34.7 |
| 23.30 | 3.81 | 4.9 |
| 24.28 | 3.66 | 8 |
| 24.76 | 3.59 | 6.9 |
| 25.25 | 3.52 | 6.2 |
| 26.57 | 3.35 | 3.2 |
| 27.05 | 3.29 | 5.4 |
| 27.68 | 3.22 | 10.2 |
| 28.55 | 3.12 | 4.9 |

Figure 24:
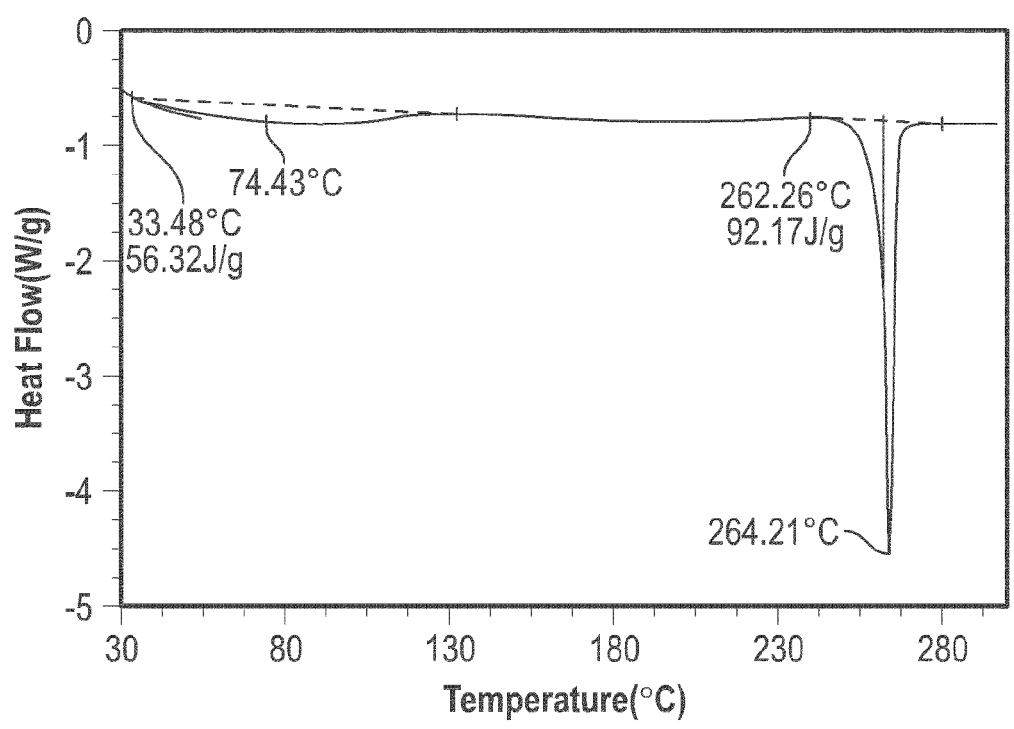
FIG. 24 shows the DSC analysis results of the crystalline form 8.

The crystalline Form 8 may further be characterized by a DSC thermogram substantially the same as that depicted in FIG. 24. As shown in FIG. 24, the crystalline Form 8 has a melting point of about 262° C.; the crystalline Form 8 has a differential scanning calorimetry thermogram with endothermic peaks at about 74° C. and at about 264° C.

Plinabulin Crystalline Form 9

Some embodiments relate to a crystalline Form 9 of plinabulin and its process of preparation.

Figure 25:
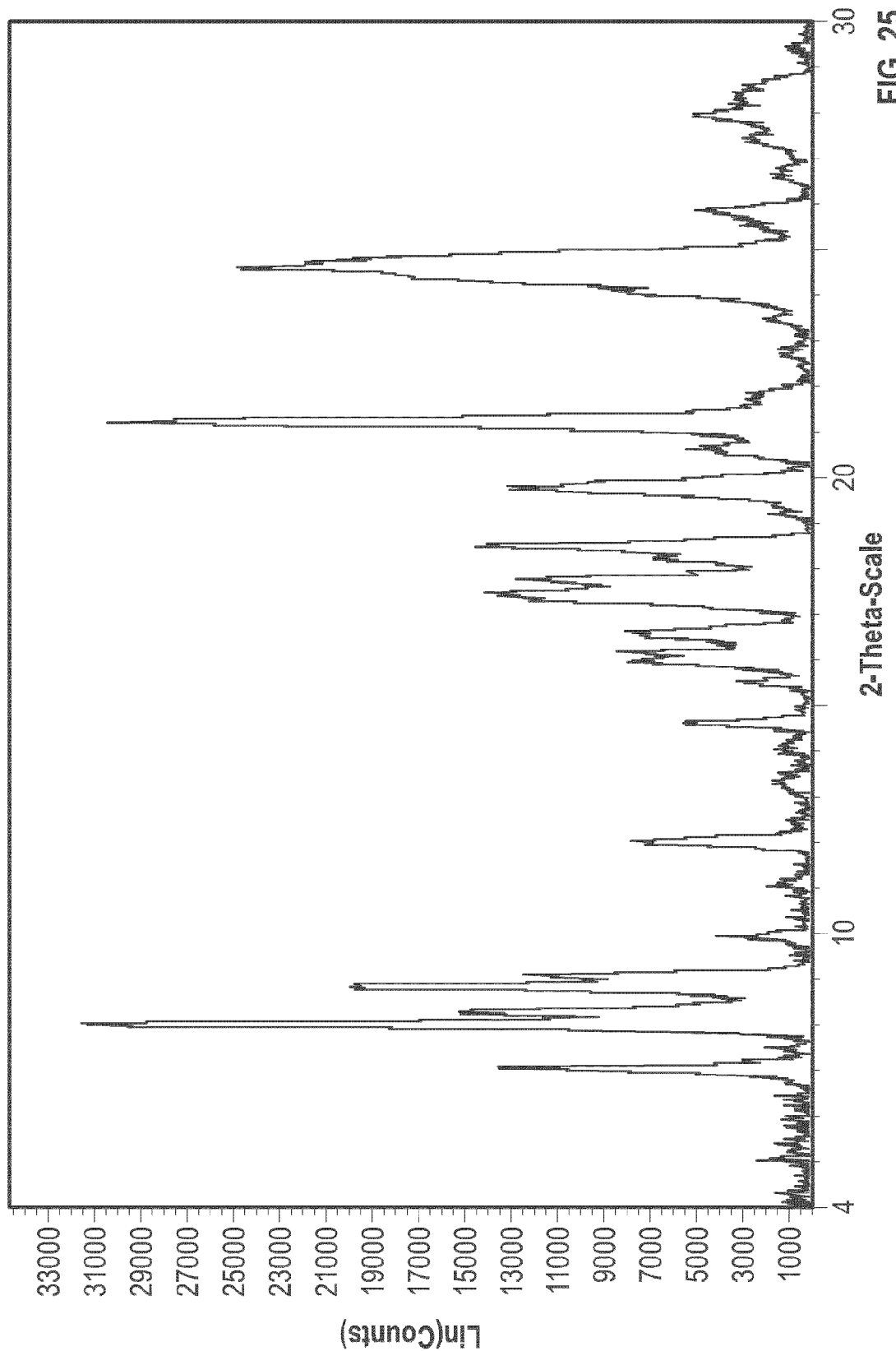
FIG. 25 is an XRPD pattern of the crystalline form 9.
Figure 26:
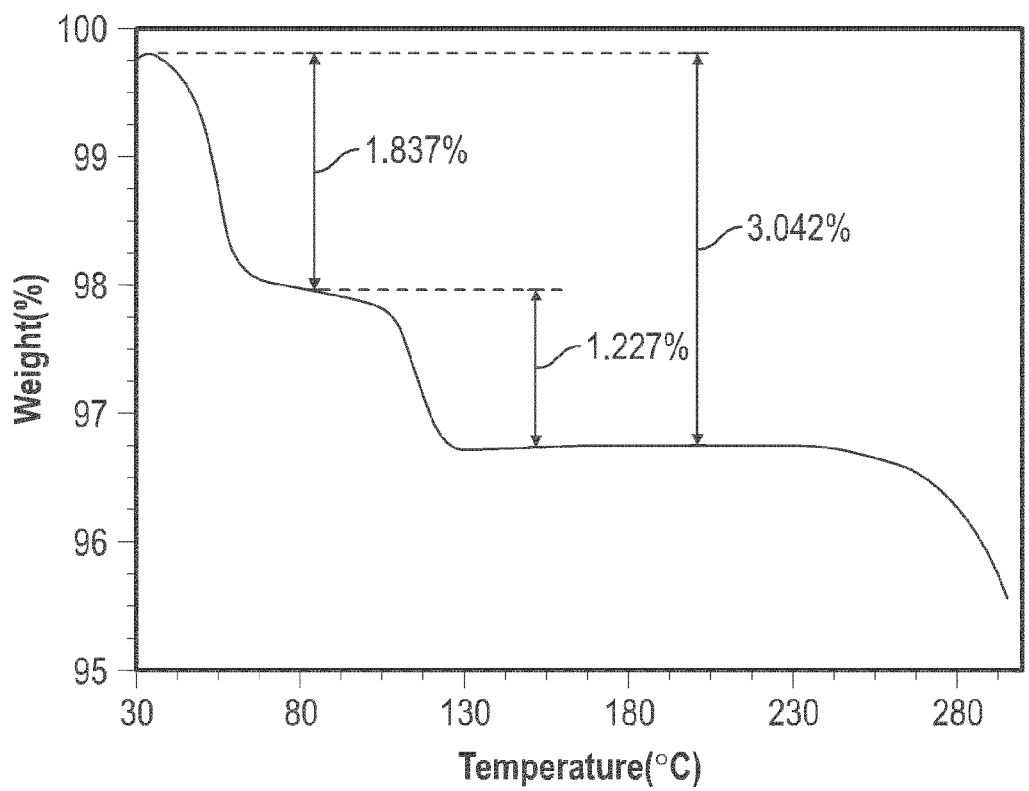
FIG. 26 shows the TGA analysis of the crystalline form 9

In some embodiments, crystalline Form 9 of plinabulin has substantially the same XRPD pattern as depicted in FIG. 25, with corresponding tabulated peak data shown in Table 9.

TABLE 9

Peak Data of PXRD pattern of crystalline Form 9

| Angle, 2θ | d spacing | Intensity, % |
|---|---|---|
| 7.03 | 12.57 | 43 |
| 8.00 | 11.04 | 100 |
| 8.27 | 10.68 | 48.3 |
| 8.84 | 9.99 | 63.1 |
| 9.08 | 9.74 | 38.4 |
| 9.94 | 8.89 | 12.8 |
| 11.11 | 7.96 | 4.4 |
| 12.03 | 7.35 | 24.6 |
| 13.32 | 6.64 | 5 |
| 14.07 | 6.29 | 5.1 |
| 14.64 | 6.05 | 17.4 |
| 15.56 | 5.69 | 10 |
| 16.02 | 5.53 | 24.2 |
| 16.21 | 5.46 | 26.6 |
| 16.57 | 5.35 | 24.4 |
| 17.45 | 5.08 | 43.7 |
| 17.74 | 4.99 | 39.4 |
| 18.24 | 4.86 | 21.5 |
| 18.50 | 4.79 | 46 |
| 19.78 | 4.49 | 41.2 |
| 20.63 | 4.30 | 17 |
| 21.23 | 4.18 | 96.5 |
| 21.80 | 4.07 | 8 |
| 22.72 | 3.91 | 4.1 |
| 23.50 | 3.78 | 6.5 |
| 24.64 | 3.61 | 78.6 |
| 25.88 | 3.44 | 14.6 |
| 26.68 | 3.34 | 4.8 |
| 27.46 | 3.25 | 9.3 |
| 27.99 | 3.19 | 16 |
| 29.45 | 3.03 | 3.2 |

Figure 27:
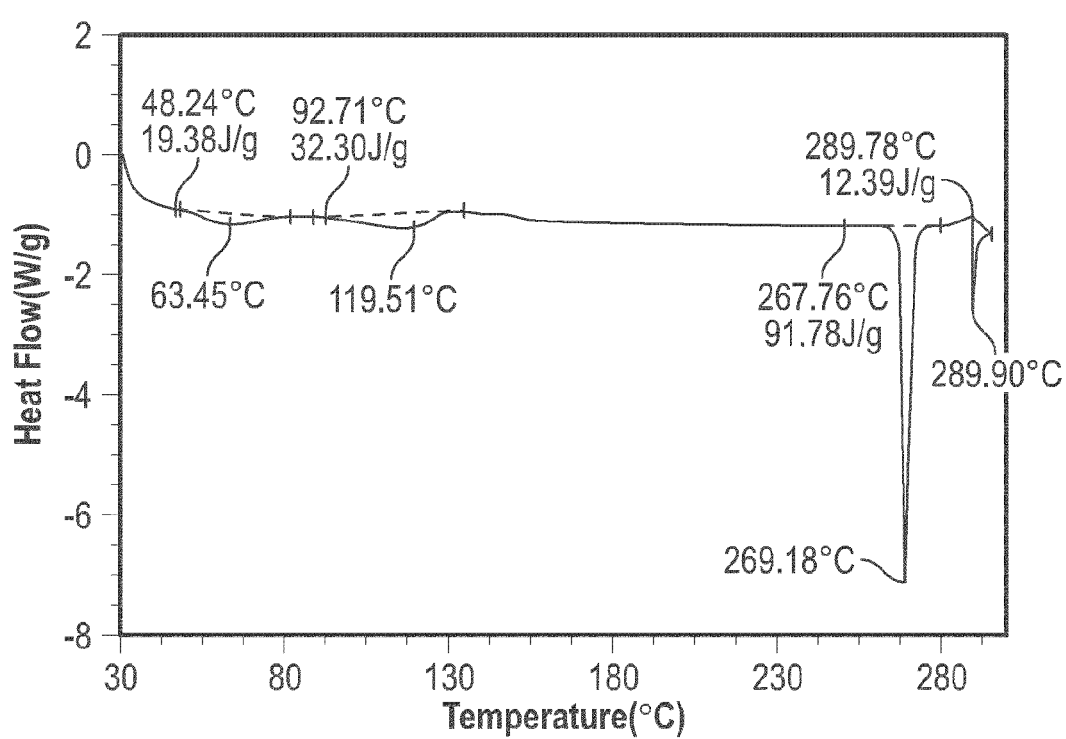
FIG. 27 shows the DSC analysis results of the crystalline form 9.

The crystalline Form 9 may further be characterized by a DSC thermogram substantially the same as that depicted in FIG. 27. As shown in FIG. 27, the crystalline Form 9 has a melting point of about 267° C.; the crystalline Form 9 has a differential scanning calorimetry thermogram with endothermic peaks at about 63° C., about 119° C., about 267° C., and about 289° C.

Conversion of Plinabulin Polymorph Forms

The plinabulin monohydrate (Form 1) is the most stable polymorph among the nine polymorph forms identified. The plinabulin monohydrate (Form 1) remains stable during the drying process and under humidity-based stability studies (stable to drying at 50° C. under vacuum over the weekend, no change in solid form on exposure to humidity higher than 95% RH for 13 days).

Figure 28:
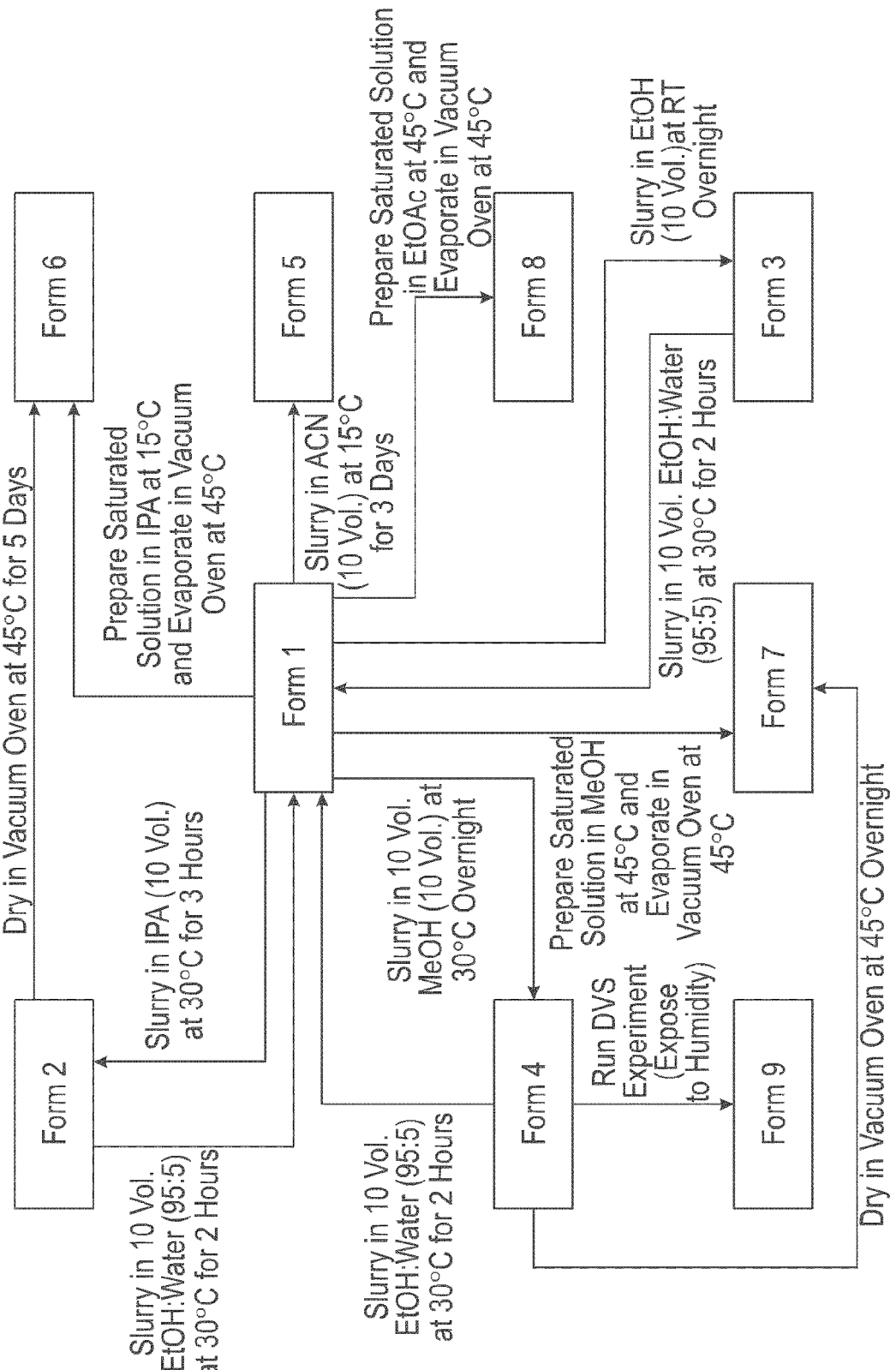
FIG. 28 shows the inter-conversion of plinabulin polymorph forms.

FIG. 28 shows how Form 1 can be converted to the other eight forms of plinabulin polymorph forms. For example, the plinabulin monohydrate (Form 1) can be converted to Form 2 by slurring Form 1 in isopropyl alcohol (about 10 times the volume of Form 1) at 30° C. for 3 hours; Form 1 can be converted to Form 3 by slurring Form 1 in ethanol (about 10 times the volume of Form 1) at room temperature for overnight; Form 1 can be converted to Form 4 by slurring Form 1 in methanol (about 10 times the volume of Form 1) at 30° C. for overnight; Form 1 can be converted to Form 5 by slurring Form 1 in acetonitrile (ACN) at 30° C. and stirring for 3 days; Form 1 can be converted to Form 6 by preparing a Form 1 saturated isopropyl alcohol solution at 15° C. and then evaporate in vacuum over at 45° C.; Form 1 can be converted to Form 7 by preparing a Form 1 saturated methanol solution at 45° C. and then evaporate in vacuum over at 45° C.; Form 1 can be converted to Form 8 by preparing a Form 1 saturated ethyl acetate (EtOAc) solution at 45° C. and then evaporate in vacuum over at 45° C.; and Form 1 can be converted to Form 9 by first converting Form 1 to Form 4 and then exposing Form 4 to moisture.

FIG. 28 also shows how other forms can be converted to Form 1. For example, Forms 2, 3, and 4 can be converted to Form 1 by slurrying these forms in a mixture of ethanol and water (95:5 by volume) (the volume of ethanol and water mixture is about 10 times of the staring polymorph forms) at 30° C. for 2 hours; Form 2 can be converted to Form 6 by drying it in vacuum oven at 45° C. for 5 days; Form 4 can be converted to Form 7 by drying it in vacuum oven at 45° C. overnight; and Form 4 can be converted to Form 9 by exposing it to high humidity.

Administration and Pharmaceutical Compositions

Some embodiments include pharmaceutical compositions comprising the plinabulin polymorph described herein and a pharmaceutically acceptable carrier. Such a composition can be administered to a subject as part of a therapeutic treatment.

In some embodiments, the composition can further include one or more pharmaceutically acceptable diluents. In some embodiments, the pharmaceutically acceptable diluent can include Kolliphor® (Polyoxyl 15 hydroxystearate). In some embodiments, the pharmaceutically acceptable diluent can include propylene glycol. In some embodiments, the pharmaceutically acceptable diluents can include kolliphor and propylene glycol. In some embodiments, the pharmaceutically acceptable diluents can include kolliphor and propylene glycol, wherein the kolliphor is about 40% by weight and propylene glycol is about 60% by weight based on the total weight of the diluents. In some embodiments, the composition can further include one or more other pharmaceutically acceptable excipients.

Standard pharmaceutical formulation techniques can be used to make the pharmaceutical compositions described herein, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of Plinabulin polymorph or pharmaceutically acceptable salts thereof; and (b) a pharmaceutically acceptable carrier, diluent, excipient or combination thereof.

Other embodiments include co-administering plinabulin polymorph and an additional therapeutic agent in separate compositions or the same composition. Thus, some embodiments include a first pharmaceutical compositions comprising: (a) a safe and therapeutically effective amount of plinabulin polymorph or pharmaceutically acceptable salts thereof and (b) a pharmaceutically acceptable carrier, diluent, excipient or combination thereof; and a second pharmaceutical composition comprising: (a) a safe and therapeutically effective amount of an additional therapeutic agent and (b) a pharmaceutically acceptable carrier, diluent, excipient or combination thereof. Some embodiments include a pharmaceutical composition comprising: (a) a safe and therapeutically effective amount of plinabulin polymorph or pharmaceutically acceptable salts thereof; (b) a safe and therapeutically effective amount of an additional therapeutic agent; and (c) a pharmaceutically acceptable carrier, diluent, excipient or combination thereof.

Administration of the pharmaceutical compositions described herein can be via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarilly, vaginally, rectally, or intraocularly. Oral and parenteral administrations are customary in treating the indications that are the subject of the preferred embodiments.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The compositions described herein are preferably provided in unit dosage form. As used herein, a "unit dosage form" is a composition containing an amount of a compound or composition that is suitable for administration to an animal, preferably a mammalian subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, although a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, sublingual, buccal, nasal, rectal, topical (including transdermal and intradermal), ocular, intracerebral, intracranial, intrathecal, intraarterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutical-active materials may be included, which do not substantially interfere with the activity of the compound or composition. The amount of carrier employed in conjunction with the compound or composition is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules (e.g., liquid gel capsule and solid gel capsule), granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, sucrose, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject composition is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium (EDTA), although other chelating agents may also be used in place or in conjunction with it.

For topical use, creams, ointments, gels, solutions or suspensions, etc., containing the composition disclosed herein are employed. Topical formulations may generally be comprised of a pharmaceutical carrier, co-solvent, emulsifier, penetration enhancer, preservative system, and emollient.

For intravenous administration, the compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

In some embodiments, a single dose of plinabulin polymorph or other therapeutic agent may be from about 5 $mg/m^2$ to about 150 $mg/m^2$ of body surface area, from about 5 $mg/m^2$ to about 100 $mg/m^2$ of body surface area, from about 10 $mg/m^2$ to about 100 $mg/m^2$ of body surface area, from about 10 $mg/m^2$ to about 80 $mg/m^2$ of body surface area, from about 10 $mg/m^2$ to about 50 $mg/m^2$ of body surface area, from about 10 $mg/m^2$ to about 40 $mg/m^2$ of body surface area, from about 10 $mg/m^2$ to about 30 $mg/m^2$ of body surface area, from about 13.5 $mg/m^2$ to about 100 $mg/m^2$ of body surface area, from about 13.5 $mg/m^2$ to about 80 $mg/m^2$ of body surface area, from about 13.5 $mg/m^2$ to about 50 $mg/m^2$ of body surface area, from about 13.5 $mg/m^2$ to about 40 $mg/m^2$ of body surface area, from about 13.5 $mg/m^2$ to about 30 $mg/m^2$ of body surface area, from about 15 $mg/m^2$ to about 80 $mg/m^2$ of body surface area, from about 15 $mg/m^2$ to about 50 $mg/m^2$ of body surface area, or from about 15 $mg/m^2$ to about 30 $mg/m^2$ of body surface area. In some embodiments, a single dose of plinabulin polymorph or other therapeutic agent may be from about 13.5 $mg/m^2$ to about 30 $mg/m^2$ of body surface area. In some embodiments, a single dose of plinabulin polymorph or other therapeutic agent may be about 5 $mg/m^2$, about 10 $mg/m^2$, about 12.5 $mg/m^2$, about 13.5 $mg/m^2$, about 15 $mg/m^2$, about 17.5 $mg/m^2$, about 20 $mg/m^2$, about 22.5 $mg/m^2$, about 25 $mg/m^2$, about 27.5 $mg/m^2$, about 30 $mg/m^2$, about 40 $mg/m^2$, about 50 $mg/m^2$, about 60 $mg/m^2$, about 70 $mg/m^2$, about 80 $mg/m^2$, about 90 $mg/m^2$, or about 100 $mg/m^2$, of body surface area.

In some embodiments, a single dose of plinabulin polymorph or other therapeutic agent may be from about 5 mg to about 300 mg, from about 5 mg to about 200 mg, from about 7.5 mg to about 200 mg, from about 10 mg to about 100 mg, from about 15 mg to about 100 mg, from about 20 mg to about 100 mg, from about 30 mg to about 100 mg, from about 40 mg to about 100 mg, from about 10 mg to about 80 mg, from about 15 mg to about 80 mg, from about 20 mg to about 80 mg, from about 30 mg to about 80 mg, from about 40 mg to about 80 mg, from about 10 mg to about 60 mg, from about 15 mg to about 60 mg, from about 20 mg to about 60 mg, from about 30 mg to about 60 mg, or from about 40 mg to about 60 mg, In some embodiments, a single dose of plinabulin polymorph or other therapeutic agent may be from about 20 mg to about 60 mg, from about 27 mg to about 60 mg, from about 20 mg to about 45 mg, or from about 27 mg to about 45 mg. In some embodiments, a single dose of plinabulin polymorph or other therapeutic agent may be about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

The administration period can be a multi-week treatment cycle as long as the tumor remains under control and the regimen is clinically tolerated. In some embodiments, a single dosage of plinabulin polymorph or other therapeutic agent can be administered once a week, and preferably once on each of day 1 and day 8 of a three-week (21 day) treatment cycle. In some embodiments, a single dosage of plinabulin polymorph or other therapeutic agent can be administered once a week, twice a week, three times per week, four times per week, five times per week, six times per week, or daily during a one-week, two-week, three-week, four-week, or five-week treatment cycle. The administration can be on the same or different day of each week in the treatment cycle.

The treatment cycle can be repeated as long as the regimen is clinically tolerated. In some embodiments, the treatment cycle is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle.

In some embodiments, the compositions described herein can be used in combination with other therapeutic agents. In some embodiments, the compositions described herein can be administered or used in combination with treatments such as chemotherapy, radiation, and biologic therapies.

EXAMPLES

Example 1

A sample of plinabulin compound was stirred in ethanol and heated to reflux. Ethanol was added in portions to maintain reflux until the entire sampled dissolved to give a clear yellow solution. A total of 124.7 g of ethanol were required to completely dissolve the sample at reflux. The solution was then allowed to cool and monitored for precipitation. A precipitate was observed when the solution was at 49° C. The mixture was reheated to reflux providing a clear yellow solution. The hot solution was transferred to a larger Erlenmeyer flask with a 9.45 g ethanol rinse (to mimic a hot filtration). To this refluxing solution was added 6.6 g of water (approximately 5% water in ethanol). This solution was allowed to cool slowly with stirring. A precipitate was observed when the solution cooled to 70° C. At this point additional water (128.6 g) was added slowly causing a large amount of solid to precipitate. The solution was allowed to cool to room temperature with stirring. The solids were filtered at 17° C. and washed three times with 20 g of water. A total of 134 g of water was added to the filtrate causing a hazy solution, an insufficient amount of solid to filter. An additional 137 g of water was added in an attempt to precipitate additional product but no additional solid was recoverable. The solid was dried at 40-45° C. for 3 days to give 4.73 g, 97.5% recovery. Analysis by XRPD showed the product to be plinabulin monohydrate (Form 1). Analysis by Karl Fischer showed the moisture level was 4.9%.

Analysis by KF after drying at 45° C. under vacuum for an additional 70 hours indicated the moisture level had decreased to 4.1%. The XRPD of this sample indicated that it was plinabulin monohydrate (Form 1). This sample was placed in a glove bag in an open container with an open container of water and the moisture level monitored. After 4 hours the moisture level was measured as 5.0%. After 18.5 hours the moisture level was measured as 4.8% and after 51 hours the KF result was 4.9%.

Example 2

A sample of plinabulin compound (4.92 g) was stirred in ethanol (147.6 g) and heated to reflux (fully soluble at 75° C.). The solution was then allowed to cool and monitored for precipitation. A precipitate was observed when the solution was at 48° C. The mixture was re-heated to reflux providing a clear yellow solution. To the hot solution was added 295 g of water (approximately twice the mass of ethanol) allowing the mixture to cool during the addition. A precipitate was observed after charging approximately 150 mL of water with the temperature at 48° C. This solution was allowed to cool to room temperature. The solids were filtered and washed three times with 20 g of water. The solid was dried at 40-45° C. for 2.5 days to give 4.82 g, 98.0% recovery. Analysis by XRPD showed the product to be a mix of plinabulin monohydrate (Forms 1) (major) and anhydrous plinabulin (Form 3) (minor). Analysis by Karl Fischer showed the moisture level was 5.0%. Analysis by KF after drying at 45° C. under vacuum for an additional 70 hours indicated the moisture level had decreased to 4.4%. The XRPD of this sample indicates it was essentially unchanged, a mixture of Forms 1 and 3 with additional peaks (at around 12.26°, 15.19° and 28.79° 2θ degrees). This sample was placed in a glove bag in an open container with an open container of water and the moisture level monitored. After 4 hours the moisture level was measured as 5.0%. After 18.5 hours the moisture level was measured as 4.9% and after 51 hours the KF result was 5.1%.

Example 3

A sample of plinabulin compound was dissolved in 1,2-propanediol with vigorous stirring or mild heating (50° C.). After 4 hours, the sample showed peaks associated with Form 3. After stirring over the weekend, the sample was slurried in water and converted entirely to plinabulin monohydrate (Form 1) with no peaks associated with crystalline Form 3 present in the XRPD scans. A similar result was seen for the experiment in ethanol/water, with very small peaks seen for Form 3 at 1 hour and 4 hours and only Form 1 observed after 66 hours.

Example 4

In a reprocessing procedure, a plinabulin compound (Form 3) was dissolved in ethanol at a ratio of 1:25 (by weight) at reflux. This solution was filtered at a temperature that was higher 50° C. and the filtrate was combined with an equal mass of water to afford the product. It may be desirable to reheat the polish-filtered ethanol solution prior to addition of the entire amount of water and add approximately 5% water (relative to ethanol) and stir this solution at approximately 70° C. to ensure conversion to Form 1. Additional water can then be added and the mixture cooled to isolate the product by filtration. The sample can be dried for an extended period to lower the moisture content as measured by Karl Fisher analysis. One sample was dried for three days resulting in a KF analysis of 4.9% moisture. Drying for an additional three days lowered the KF result to 4.1%.

Exposing the dry product to a humid environment raised the moisture level to approximately 5% where it appeared to remain stable. One sample with 4.1% moisture was exposed to an open container of water in a glove bag for 4 hours, raising the moisture level to 5.0%. After an additional 14.5 hours in this environment the moisture level in the sample was measured as 4.8%. After a total of 51 hours the KF result was 4.9%.

Example 5

A batch of plinabulin having a KF analysis of about 3.1% for water content was added to a mixture of kolliphor (40% wt) and propylene glycol (60% wt). Insoluble particles were formed in the solution, and it was determined that the insoluble particles were anhydrous plinabulin (Form 3). The batch was reprocessed according to the steps described in FIG. 29 to form the plinabulin monohydrate (Form 1). Analysis by KF showed that the water content of the reprocessed plinabulin was about 5.1%, which is consistent with the theoretical water content for the monohydrate. The plinabulin monohydrate (Form 1) dissolved completely in a mixture of kolliphor (40% wt) and propylene glycol (60% wt) and no insoluble particles were formed in the solution. Therefore, the plinabulin monohydrate (Form 1) showed better solubility than plinabulin compositions that contain anhydrous plinabulin (Form 3).

Example 6

Figure 2:
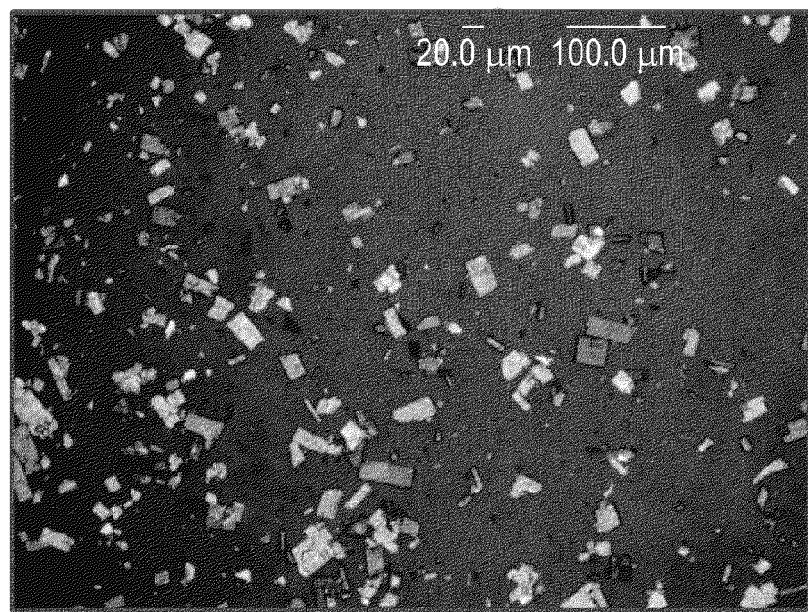
FIG. 2 shows a polarized light microscopy (PLM) image of a sample containing the crystalline form of plinabulin monohydrate.

The plinabulin monohydrate (Form 1 crystalline) was characterized by XRPD (crystalline, FIG. 1), optical microscopy (FIG. 2), DSC (FIG. 3A), TGA (FIG. 3B), and KF.

The DSC data were collected using a TA Instruments Q10 DSC. Typically, samples (~2 mg) were placed in hermetic alodined aluminum sample pans and scanned from 30 to 300° C. at a rate of 10° C./min under a nitrogen purge of 50 mL/min. The TGA data were collected using a TA Instruments TGA Q500. Typically, samples (~10 mg) were placed in an open, pre-tared aluminum sample pan and scanned from 30 to 300° C. at a rate of 10° C./min using a nitrogen purge at 60 mL/min. The X-ray powder diffraction patterns were obtained using a Bruker D8 Advance equipped with a Cu Kα radiation source (1.54° A), a 9-position sample holder and a LYNXEYE Super Speed Detector. Typically, the duration of each scan was 180 seconds and the 2θ range was 4 to 40°. Samples were placed on zero-background, silicon plate holders. Samples were analyzed using an Aquadyne DVS-2 gravimetric water sorption analyzer. The relative humidity was adjusted between 2-95% and the weight of sample was continuously monitored and recorded.

The XRPD showed that the material is crystalline. The DSC data showed a broad endotherm (peak max at 141° C., likely water loss), a small exothermic event (peak max 164° C.) and a sharp endothermic event (peak max 268° C.). TGA indicated loss of 5.26% of mass at about 130° C. (likely water loss). KF analysis also showed that the material contains water at 5.25 weight %.

A sample of plinabulin monohydrate (Form 1) was placed in a vacuum oven at 50° C. overnight and over the weekend. The sample remained stable during the drying studies and no change in weight occurred during the drying process.

Figure 3C:
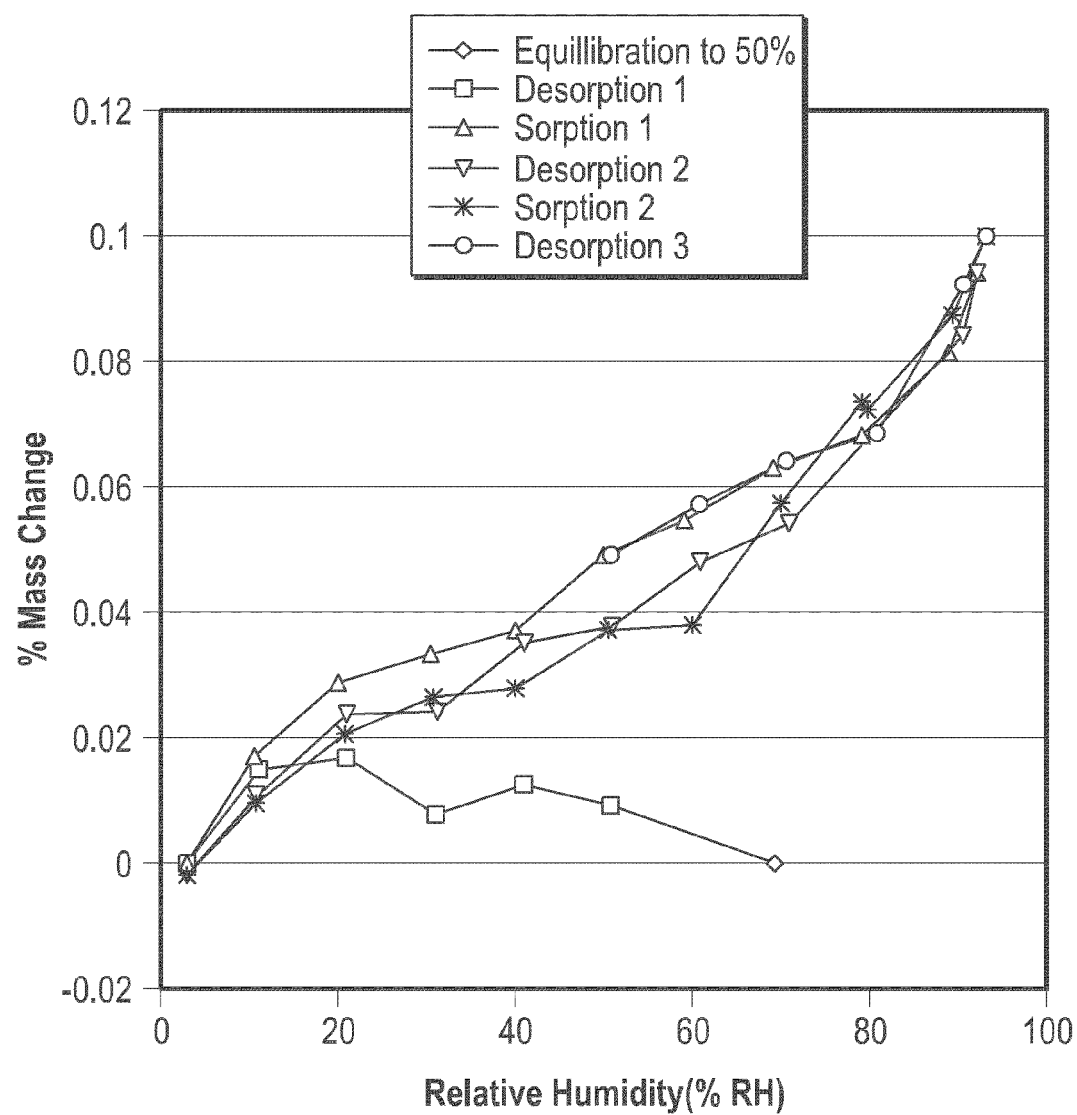
FIG. 3C shows the Dynamic Vapor Sorption (DVS) isotherm plot.

A DVS experiment was run on the plinabulin monohydrate (Form 1). The sample gained ~0.1% mass at 95% RH which was lost on drying to 0% RH without hysteresis. The post-DVS sample was analyzed by XRPD which confirmed that no transformation had taken place. FIG. 3C shows the DVS isotherm plot. The XRPD pattern of the pre-DVS sample (Form 1 plinabulin monohydrate) overlays with the XRPD patterns of the post-DVS sample (Form 1 plinabulin monohydrate).

The DVS test of Form 2 solids showed that the Form 2 sample lost about 7% mass at about 80% RH, and the post-DVS sample differed from the pre-DVS sample based on the XRPD pattern analysis.

The DVS test of Form 3 solids showed that the Form 3 sample lost about 0.2% mass at 90% RH, and the post-DVS sample differed from the pre-DVS sample based on the XRPD pattern analysis.

The DVS test of Form 4 solids showed that the Form 3 sample lost mass in the test. The post-DVS sample differed from the pre-DVS sample based on the XRPD pattern analysis.

The plinabulin monohydrate (Form 1) remained stable during the DVS and drying tests. In comparison, other polymorph forms were unstable and showed weight change during the DVS tests. The test results have shown that Form 1 is more stable than the other polymorph forms.

Example 7

A plinabulin compound was slurried in 15 different solvents/solvent mixtures as shown in Table 9 at 15° C. and 45° C. for 3 days for gravimetric solubility measurement. About 70 mg of solid was added to a vial for each experiment followed by addition of 0.7 mL of the respective solvents. Next, the slurry was centrifuged and the supernatant was added to pre-weighed vials and evaporated to dryness under vacuum. The vials with remaining solids were weighed again to calculate the solubility. The compound is highly soluble in THF and had moderate to low solubility in the other solvents tested. The solubility data is shown in Table 10.

TABLE 10

Gravimetric solubility data of plinabulin monohydrate in various solvents.

| Sample No. | Solvent | Solubility at 15° C. in mg/mL | Solubility at 45° C. in mg/mL |
|---|---|---|---|
| 1 | Heptane | <1 | 3 |
| 2 | Toluene | 1 | 7 |
| 3 | MTBE | <1 | 5 |
| 4 | EtOAc | 3 | 8 |
| 5 | THF | 40 | 96 |
| 6 | IPA | 1 | 7 |
| 7 | Acetone | 11 | 20 |
| 8 | EtOH | 5 | 13 |
| 9 | MeOH | 5 | 13 |
| 10 | ACN | 3 | 7 |
| 11 | Water | <1 | <1 |
| 12 | MEK | 11 | 23 |
| 13 | DCM | 2 | N/A |
| 14 | Acetone:water (95:5) | 6 | 16 |
| 15 | EtOH:water (95:5) | 4 | 13 |

During gravimetric solubility analysis, the plinabulin monohydrate (Form 1) was slurried in various solvents at 15° C. and at 45° C. After centrifugation, the solids obtained were analyzed as wet cake by XRPD. The samples which were not Form 1 were dried in a vacuum oven and reanalyzed by XRPD. Forms 2, 3, 4, 5, 6, and 7 were observed. These results are shown in Table 11.

TABLE 11

XRPD results of slurry experiments in various solvents before and after drying

| No. | Solvent | 15° C. slurry wet XRPD | 45° C. slurry wet XRPD | 15° C. slurry dry XRPD | 45° C. slurry dry XRPD |
|---|---|---|---|---|---|
| 1 | Heptane | Form 1 | Form 1 | N/A | N/A |
| 2 | Toluene | Form 1 | Form 1 | N/A | N/A |
| 3 | MTBE | Form 1 | Form 1 | N/A | N/A |
| 4 | EtOAc | Form 1 | Form 1 + 3 | N/A | Still Form 1 + 3 |
| 5 | THF | Form 1 | Form 1 + 3 | N/A | Still Form 1 + 3 |
| 6 | IPA | Form 2 | Form 1 + 2 | Form 6 | Form 6 + 2 |

TABLE 11-continued

XRPD results of slurry experiments in various solvents before and after drying

| No. | Solvent | 15° C. slurry wet XRPD | 45° C. slurry wet XRPD | 15° C. slurry dry XRPD | 45° C. slurry dry XRPD |
|---|---|---|---|---|---|
| 7 | Acetone | Form 1 + 3 | Form 3 | Still Form 1 + 3 | Still Form 3 |
| 8 | EtOH | Form 3 | Form 3 | Still Form 3 | Still Form 3 |
| 9 | MeOH | Form 1 + 4 | Form 4 | Still Form 1 + 4 | Form 7 |
| 10 | ACN | Form 5 | Form 3 | Still Form 5 | N/A |
| 11 | Water | Form 1 | Form 1 | N/A | N/A |
| 12 | MEK | Form 1 | Form 3 | N/A | N/A |
| 13 | DCM | Form 1 | N/A | N/A | N/A |
| 14 | Acetone:water (95:5) | Form 1 | Form 1 | N/A | N/A |
| 15 | EtOH:water (95:5) | Form 1 | Form 1 | N/A | N/A |

Evaporation crystallization experiments were setup by evaporating (at room temperature) solutions of the plinabulin monohydrate in various solvents. These solutions were obtained during the gravimetric solubility analysis at 15° C. and at 45° C. and were of different concentrations. The solids obtained were analyzed by XRPD. Form 8 was observed. These results are shown in Table 12.

TABLE 12

XRPD results of evaporation crystallization experiments

| No. | Solvent | Evaporation of 15° C. solubility samples | Evaporation of 45° C. solubility samples |
|---|---|---|---|
| 1 | Heptane | Not enough solids | Not enough solids |
| 2 | Toluene | Not enough solids | Not enough solids |
| 3 | MTBE | Not enough solids | Not enough solids |
| 4 | EtOAc | Not enough solids | Form 8 |
| 5 | THF | Form 6 | Form 8 |
| 6 | IPA | Not enough solids | Form 6 |
| 7 | Acetone | Form 3 + 6 | Form 8 |
| 8 | EtOH | Not enough solids | Form 3 |
| 9 | MeOH | Mostly amorphous w/Form 8 peak | Form 7 |
| 10 | ACN | Not enough solids | Form 3 |
| 11 | Water | Not enough solids | Not enough solids |
| 12 | MEK | Form 3 + 6 | Form 3 |
| 13 | DCM | Not enough solids | N/A |
| 14 | Acetone:water (95:5) | Form 8 | Form 8 |
| 15 | EtOH:water (95:5) | Low Crystallinity Form 6 | Form 1 |

Six cooling crystallization experiments and one slurry experiment were carried out. The results of these experiments are shown in Table 13.

TABLE 13

XRPD results of cooling crystallization experiments

| | Solvent | Procedure | XRPD |
|---|---|---|---|
| 1 | THF | 100 mg solids dissolved in 10 vol. solvent at 60° C. Cooled naturally to RT and stirred for 2 hours. Cooled to 5° C. using a chiller and stirred for 3 hours. Crystallized. | Form 1 + 5 |
| 2 | THF:acetone 1:1 | 100 mg solids dissolved in 16 vol. solvent at 60° C. Cooled naturally to RT and stirred for 2 hours. Cooled to 5° C. using a chiller and stirred overnight. Crystallized. | Form 1 |
| 3 | THF:EtOH 1:1 | 100 mg solids dissolved in 11 vol. solvent at 60° C. Cooled naturally to RT and stirred for 2 hours. Cooled to 5° C. using a chiller and stirred for 2 hours. Crystallized. | Form 3 |
| 4 | THF:MeOH 1:1 | 100 mg solids dissolved in 8 vol. solvent at 60° C. Cooled naturally to RT and stirred for 2 hours. Cooled to 5° C. using a chiller. Crystallized at 12° C. | Form 4 |
| 5 | THF:water 1:1 | 100 mg solids did not dissolve in 20 vol. solvent at 60° C. Cooled naturally to RT and stirred overnight. | Form 1 |
| 6 | THF:MEK (methyl ethyl ketone) 1:1 | 100 mg solids dissolved in 20 vol. solvent at 60° C. Cooled naturally to RT and stirred for 2 hours. Cooled to 5° C. using a chiller and stirred for 2 hours. Crystallized. | Form 1 |

Example 8

The various crystalline forms were tested for conversion to other forms at a 200 mg scale.

A Form 3 scale up experiment was carried out at the 200 mg scale by slurrying Form 1 solids in 2 mL ethanol at room temperature overnight to produce Form 3.

A Form 2 scale up experiment was carried out at the 200 mg scale by slurrying Form 1 solids in 2 mL isopropyl alcohol at 30° C. overnight.

A Form 4 scale up experiment was carried out at the 200 mg scale by slurrying Form 1 solids in 2 mL MeOH at 30° C. overnight.

Form 3 solids were slurried in a 95:5 EtOH:water mixture at 30° C. for 2 hours and analyzed by XRPD to show conversion to Form 1.

Form 2 solids were slurried (2071-16-1) in a 95:5 EtOH:water mixture at 30° C. for 2 hours and analyzed by XRPD to show conversion to Form 1.

Form 4 solids were slurried in a 95:5 EtOH:water mixture at 30° C. for 2 hours and analyzed by XRPD to show conversion to Form 1.

The plinabulin monohydrate (Form 1) remained stable when dried at 50° C. under vacuum over the weekend. There was no change in solid form when form 1 was exposed to high humidity (>95% RH) for 13 days. Form 1 was shown to be stable during the manufacturing process including the drying process. Form 1 was also stable under various humidity conditions. On the other hand, the crystalline forms converted to Form I monohydrate when exposed to moisture. Therefore, Form 1 is the most stable crystalline form and the most viable form for manufacturing process.

What is claimed is:

1. A sterile container, comprising a plinabulin monohydrate in crystalline solid form, wherein the plinabulin monohydrate exhibits an X-ray powder diffraction pattern comprising at least three characteristic peaks selected from the group consisting of peaks at approximately 8.1°, 13.1°, 16.3°, 23.9°, 24.2°, 24.5°, and 26.6° 2θ.

2. A process of preparing a plinabulin monohydrate in crystalline form comprising the steps of:
combining plinabulin and a first solvent system to form a first mixture, wherein the first solvent system is water, alcohol, or a mixture of water and alcohol, and wherein the alcohol, if present, is selected from the group consisting of methanol, ethanol, isopropyl alcohol, tert-butyl alcohol, n-butyl alcohol, and any mixtures thereof;
heating the first mixture to a temperature in the range of about 50° C. to 90° C.; and
cooling the first mixture to form a first precipitate, wherein the plinabulin monohydrate exhibits an X-ray powder diffraction pattern comprising at least three characteristic peaks selected from the group consisting of peaks at approximately 8.1°, 13.1°, 16.3°, 23.9°, 24.2°, 24.5°, and 26.6° 2θ.

3. The process of claim 2, the first solvent system comprises ethanol.

4. The process of claim 2, wherein the heating step comprises:
refluxing the first mixture; or
heating the first mixture to a temperature in the range of about 70° C. to 78° C.

5. The process of claim 2, further comprising, prior to the cooling step, maintaining the first mixture at a temperature in the range of about 70° C. to 78° C. for about 1 hour.

6. The process of claim 2, wherein the cooling step comprises at least one of:
adding water to the first mixture to produce the first precipitate; and
stirring the first mixture for at least 4 hours.

7. The process of claim 2, wherein the heating step comprises heating the first mixture to a temperature of at least 65° C., and wherein the cooling step comprises cooling the first mixture to a temperature in the range of about 50° C. to 60° C.

8. The process of claim 2, further comprising one or more steps each independently selected from the group consisting of:
filtering the heated first mixture prior to the first cooling step;
filtering the first precipitate;
washing the first precipitate; and
analyzing the first precipitate using X-ray powder diffraction analysis.

9. The process of claim 2, further comprising the additional steps of:
combining the first precipitate and a second solvent to form a second mixture, wherein the second solvent is water, alcohol, or a mixture of water and alcohol, and wherein the alcohol, if present, is selected from the group consisting of methanol, ethanol, isopropyl alcohol, tert-butyl alcohol, n-butyl alcohol, and mixtures thereof;
heating the second mixture to a temperature in the range of about 50° C. to 90° C.;
cooling the second mixture to a temperature in the range of about 15° C. to 30° C. to form a second precipitate;
filtering the second precipitate; and
washing the second precipitate.

10. The process of claim 9, wherein the second solvent is ethanol.

11. The process of claim 9, wherein the further heating step comprises:
refluxing the second mixture; or
heating the second mixture to a temperature in the range of about 70° C. to 78° C.

12. The process of claim 9, further comprising, prior to the further cooling step, maintaining the second mixture at a refluxing temperature for about 1 hour.

13. The process of claim 9, wherein the further cooling step comprises at least one of:
adding water to the second mixture to produce the second precipitate; and
stirring the second mixture for at least 4 hours.

14. The process of claim 9, further comprising the following steps:
washing the first precipitate with an alcohol, selected from the group consisting of methanol, ethanol, isopropyl alcohol, tert-butyl alcohol, n-butyl alcohol, and mixtures thereof;
collecting the alcohol wash; and
adding the collected alcohol wash to the second mixture prior to the further heating step.

15. The process of claim 9, further comprising one or more steps each independently selected from the group consisting of:
drying the second precipitate; and
analyzing the second precipitate using X-ray powder diffraction analysis.

16. The process of claim 9, wherein the additional combining step, the additional cooling step, and the filtering step are repeated one or more times based on the amount of plinabulin in the second precipitate.

17. A process of preparing a plinabulin monohydrate in crystalline form, comprising mixing plinabulin, ethanol and water to form a mixture, wherein the plinabulin monohydrate exhibits an X-ray powder diffraction pattern comprising at least three characteristic peaks selected from the group consisting of peaks at approximately 8.1°, 13.1°, 16.3°, 23.9°, 24.2°, 24.5°, and 26.6° 2θ.

18. The process of claim 17, wherein the volume ratio of ethanol to water is in the range of about 15:1 to about 25:1.

19. The process of claim 17, wherein the process is performed at a temperature in the range of about 20° C. to about 40° C.

20. The process of claim 17, further comprising stirring the mixture for at least 2 hours.

* * * * *

UNITED STATES PATENT AND TRADEMARK OFFICE
CERTIFICATE OF CORRECTION

PATENT NO. : 10,550,104 B2
APPLICATION NO. : 16/212386
DATED : February 4, 2020
INVENTOR(S) : Lan Huang It is certified that error appears in the above-identified patent and that said Letters Patent is hereby corrected as shown below:

On the Title Page

On Page 2, Column 2, Item (56), Line 6, under Other Publications, delete "Ariloxy" and insert --Aryloxy--.

On Page 2, Column 2, Item (56), Line 27, under Other Publications, delete "thereapy:" and insert --therapy:--.

On Page 3, Column 2, Item (56), Line 7, under Other Publications, delete "Viro" and insert --Vitro--.

On Page 3, Column 2, Item (56), Line 16, under Other Publications, delete "eininge" and insert --einige--.

On Page 3, Column 2, Item (56), Line 26, under Other Publications, delete "Kiketopiperazine" and insert --Diketopiperazine--.

On Page 4, Column 1, Item (56), Line 17, under Other Publications, delete "Phospatases" and insert --Phosphatases--.

On Page 4, Column 2, Item (56), Line 47, under Other Publications, delete "Purifiied" and insert --Purified--.

In the Specification

In Column 2, Line 36, delete "5" and insert --5.--.

In Column 2, Line 40, delete "6" and insert --6.--.

In Column 2, Line 44, delete "7" and insert --7.--.

Signed and Sealed this
Thirty-first Day of May, 2022

Katherine Kelly Vidal
*Director of the United States Patent and Trademark Office*

CERTIFICATE OF CORRECTION (continued)
U.S. Pat. No. 10,550,104 B2

In Column 2, Line 52, delete "9" and insert --9.--.

In Column 7, Line 29, delete "precipitate" and insert --precipitate.--.

In Column 16, Line 23, delete "croscarmelose;" and insert --croscarmellose;--.

In Column 18, Line 57 (approx.), delete "mg," and insert --mg.--.

In Column 21, Line 29 (approx.), delete "20" and insert --2O--.

In Column 21, Line 53, below "monohydrate)." insert --The plinabulin monohydrate (Form 1) sample was placed in a high humidity environment for 13 days and remained stable with no change in mass. The pre-DYS and post-DYS samples showed no change in the XRPD pattern.--.

In Column 25, Line 28, delete "I" and insert --1--.